US012778749B2

(12) United States Patent
Syed et al.

(10) Patent No.: US 12,778,749 B2
(45) Date of Patent: Nov. 3, 2026

(54) PROSTHETIC VALVE DELIVERY SYSTEM

(71) Applicant: EDWARDS LIFESCIENCES CORPORATION, Irvine, CA (US)

(72) Inventors: Asim Minhaj Syed, Irvine, CA (US); Timothy Lee Humphrey, Anaheim, CA (US); Dustin P. Armer, Costa Mesa, CA (US); Eason Michael Abbott, Santa Monica, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 685 days.

(21) Appl. No.: 18/182,092

(22) Filed: Mar. 10, 2023

(65) Prior Publication Data

US 2023/0210658 A1 Jul. 6, 2023

Related U.S. Application Data

(63) Continuation of application No. PCT/US2021/052669, filed on Sep. 29, 2021.

(60) Provisional application No. 63/085,901, filed on Sep. 30, 2020.

(51) Int. Cl.

| | |
|---|---|
| ***A61F 2/24*** | (2006.01) |
| ***A61M 25/00*** | (2006.01) |
| ***A61M 25/01*** | (2006.01) |
| ***A61M 25/10*** | (2013.01) |

(52) U.S. Cl.

CPC ... *A61F 2/2433* (2013.01); *A61M 2025/0004* (2013.01); *A61M 25/0136* (2013.01); *A61M 25/10* (2013.01)

(58) Field of Classification Search

CPC .... A61F 2/9517; A61F 2/2418; A61F 2/2436; A61F 2/2433; A61F 2/2466; A61M 25/0136; A61M 2025/0681; A61M 2025/1081; A61M 25/0102; A61M 25/10; A61M 2025/0004

See application file for complete search history.

(56) References Cited

U.S. PATENT DOCUMENTS

| | | | |
|---|---|---|---|
| 519,297 | A | 5/1894 | Bauer |
| 4,035,849 | A | 7/1977 | Angell et al. |
| 4,592,340 | A | 6/1986 | Boyles |

(Continued)

FOREIGN PATENT DOCUMENTS

| | | | |
|---|---|---|---|
| CN | 216876729 | U | 7/2022 |
| DE | 19532846 | A1 | 3/1997 |

(Continued)

*Primary Examiner* — Thomas C Barrett
*Assistant Examiner* — Mikail A Mannan
(74) *Attorney, Agent, or Firm* — Klarquist Sparkman LLP

(57) ABSTRACT

Embodiments of a delivery apparatus for implanting a prosthetic valve are disclosed. The delivery apparatus can include a handle, a first shaft extending from a distal end of the handle, a second shaft extending through a lumen of the first shaft and the handle, and a gripper located proximal to a proximal end of the handle. A proximal end of the second shaft can be connected to the gripper, and the gripper can be axially moveable relative to the handle such that axial movement of the gripper causes corresponding axial movement of the second shaft relative to the first shaft. The gripper can have a bottom surface that is substantially coplanar with a bottom surface of the handle.

22 Claims, 13 Drawing Sheets

(56) References Cited

U.S. PATENT DOCUMENTS

| | | | |
|---|---|---|---|
| 4,955,895 | A | 9/1990 | Sugiyama et al. |
| 4,994,077 | A | 2/1991 | Dobben |
| 5,059,177 | A | 10/1991 | Towne et al. |
| 5,176,698 | A | 1/1993 | Burns et al. |
| 5,192,297 | A | 3/1993 | Hull |
| 5,266,073 | A | 11/1993 | Wall |
| 5,325,845 | A | 7/1994 | Adair |
| 5,358,496 | A | 10/1994 | Ortiz et al. |
| 5,411,552 | A | 5/1995 | Andersen et al. |
| 5,554,185 | A | 9/1996 | Block et al. |
| 5,591,195 | A | 1/1997 | Taheri et al. |
| 5,599,305 | A | 2/1997 | Hermann et al. |
| 5,632,760 | A | 5/1997 | Sheiban et al. |
| 5,639,274 | A | 6/1997 | Fischell et al. |
| 5,728,068 | A | 3/1998 | Leone et al. |
| 5,749,890 | A | 5/1998 | Shaknovich |
| 5,782,809 | A | 7/1998 | Umeno et al. |
| 5,824,044 | A | 10/1998 | Quiachon et al. |
| 5,840,081 | A | 11/1998 | Andersen et al. |
| 5,908,405 | A | 6/1999 | Imran et al. |
| 5,916,147 | A | 6/1999 | Boury |
| 5,944,690 | A | 8/1999 | Falwell et al. |
| 5,961,536 | A | 10/1999 | Mickley et al. |
| 5,968,068 | A | 10/1999 | Dehdashtian et al. |
| 6,019,777 | A | 2/2000 | Mackenzie |
| 6,027,510 | A | 2/2000 | Alt |
| 6,033,381 | A | 3/2000 | Kontos |
| 6,143,016 | A | 11/2000 | Bleam et al. |
| 6,162,208 | A | 12/2000 | Hipps |
| 6,168,614 | B1 | 1/2001 | Andersen et al. |
| 6,174,327 | B1 | 1/2001 | Mertens et al. |
| 6,217,585 | B1 | 4/2001 | Houser et al. |
| 6,235,050 | B1 | 5/2001 | Quiachon et al. |
| 6,251,092 | B1 | 6/2001 | Qin et al. |
| 6,379,372 | B1 | 4/2002 | Dehdashtian et al. |
| 6,383,171 | B1 | 5/2002 | Gifford et al. |
| 6,454,799 | B1 | 9/2002 | Schreck |
| 6,458,153 | B1 | 10/2002 | Bailey et al. |
| 6,461,382 | B1 | 10/2002 | Cao |
| 6,471,672 | B1 | 10/2002 | Brown et al. |
| 6,500,147 | B2 | 12/2002 | Omaleki et al. |
| 6,514,228 | B1 | 2/2003 | Hamilton et al. |
| 6,527,979 | B2 | 3/2003 | Constantz et al. |
| 6,579,305 | B1 | 6/2003 | Lashinski |
| 6,582,462 | B1 | 6/2003 | Andersen et al. |
| 6,652,578 | B2 | 11/2003 | Bailey et al. |
| 6,730,118 | B2 | 5/2004 | Spenser et al. |
| 6,733,525 | B2 | 5/2004 | Yang et al. |
| 6,764,504 | B2 | 7/2004 | Wang et al. |
| 6,767,362 | B2 | 7/2004 | Schreck |
| 6,830,584 | B1 | 12/2004 | Seguin |
| 6,893,460 | B2 | 5/2005 | Spenser et al. |
| 6,908,481 | B2 | 6/2005 | Cribier |
| 7,011,094 | B2 | 3/2006 | Rapacki et al. |
| 7,018,406 | B2 | 3/2006 | Seguin et al. |
| 7,018,408 | B2 | 3/2006 | Bailey et al. |
| 7,137,993 | B2 | 11/2006 | Acosta et al. |
| 7,276,084 | B2 | 10/2007 | Yang et al. |
| 7,318,278 | B2 | 1/2008 | Zhang et al. |
| 7,320,702 | B2 | 1/2008 | Hammersmark et al. |
| 7,320,704 | B2 | 1/2008 | Lashinski et al. |
| 7,374,571 | B2 | 5/2008 | Pease et al. |
| 7,393,360 | B2 | 7/2008 | Spenser et al. |
| 7,435,257 | B2 | 10/2008 | Lashinski et al. |
| 7,510,575 | B2 | 3/2009 | Spenser et al. |
| 7,585,321 | B2 | 9/2009 | Cribier |
| 7,594,926 | B2 | 9/2009 | Linder et al. |
| 7,597,709 | B2 | 10/2009 | Goodin |
| 7,618,446 | B2 | 11/2009 | Andersen et al. |
| 7,780,723 | B2 | 8/2010 | Taylor |
| 7,785,366 | B2 | 8/2010 | Maurer et al. |
| 7,959,661 | B2 | 6/2011 | Hijlkema et al. |
| 8,029,556 | B2 | 10/2011 | Rowe |
| 8,167,932 | B2 | 5/2012 | Bourang et al. |
| RE43,882 | E | 12/2012 | Hopkins et al. |
| 8,449,606 | B2 | 5/2013 | Eliasen et al. |
| 8,475,523 | B2 | 7/2013 | Duffy |
| 8,568,472 | B2 | 10/2013 | Marchand et al. |
| 9,061,119 | B2 | 6/2015 | Le et al. |
| 9,119,716 | B2 | 9/2015 | Lee et al. |
| 9,795,477 | B2 | 10/2017 | Tran et al. |
| 11,273,038 | B2 | 3/2022 | Tang et al. |
| 2001/0002445 | A1 | 5/2001 | Vesely |
| 2001/0007082 | A1 | 7/2001 | Dusbabek et al. |
| 2002/0032481 | A1 | 3/2002 | Gabbay |
| 2002/0058995 | A1 | 5/2002 | Stevens |
| 2002/0165461 | A1 | 11/2002 | Hayzelden et al. |
| 2003/0040792 | A1 | 2/2003 | Gabbay |
| 2003/0050694 | A1 | 3/2003 | Yang et al. |
| 2003/0120341 | A1 | 6/2003 | Shennib et al. |
| 2004/0093061 | A1 | 5/2004 | Acosta et al. |
| 2004/0133263 | A1 | 7/2004 | Dusbabek et al. |
| 2004/0143197 | A1 | 7/2004 | Soukup et al. |
| 2004/0186563 | A1 | 9/2004 | Lobbi |
| 2004/0186565 | A1 | 9/2004 | Schreck |
| 2004/0260389 | A1 | 12/2004 | Case et al. |
| 2005/0080474 | A1 | 4/2005 | Andreas et al. |
| 2005/0096736 | A1 | 5/2005 | Osse et al. |
| 2005/0137689 | A1 | 6/2005 | Salahieh et al. |
| 2005/0149160 | A1 | 7/2005 | McFerran |
| 2005/0203614 | A1 | 9/2005 | Forster et al. |
| 2005/0203617 | A1 | 9/2005 | Forster et al. |
| 2005/0245894 | A1 | 11/2005 | Zadno-Azizi |
| 2005/0272975 | A1* | 12/2005 | McWeeney ............ A61B 1/307 600/172 |
| 2006/0025857 | A1 | 2/2006 | Bergheim et al. |
| 2006/0282150 | A1 | 12/2006 | Olson et al. |
| 2007/0005131 | A1 | 1/2007 | Taylor |
| 2007/0073389 | A1 | 3/2007 | Bolduc et al. |
| 2007/0088431 | A1 | 4/2007 | Bourang et al. |
| 2007/0100356 | A1 | 5/2007 | Lucatero et al. |
| 2007/0112422 | A1 | 5/2007 | Dehdashtian |
| 2007/0156225 | A1 | 7/2007 | George et al. |
| 2007/0203575 | A1 | 8/2007 | Forster et al. |
| 2007/0219612 | A1 | 9/2007 | Andreas et al. |
| 2007/0239254 | A1 | 10/2007 | Chia et al. |
| 2007/0244546 | A1 | 10/2007 | Francis |
| 2007/0265700 | A1 | 11/2007 | Eliasen et al. |
| 2007/0270932 | A1* | 11/2007 | Headley .................... A61F 2/95 623/1.11 |
| 2008/0065011 | A1 | 3/2008 | Marchand et al. |
| 2008/0103520 | A1 | 5/2008 | Selkee |
| 2008/0109065 | A1* | 5/2008 | Bowe ........................ A61F 2/95 623/1.13 |
| 2008/0125853 | A1 | 5/2008 | Bailey et al. |
| 2008/0294230 | A1 | 11/2008 | Parker |
| 2009/0024428 | A1 | 1/2009 | Hudock, Jr. |
| 2009/0069889 | A1 | 3/2009 | Suri et al. |
| 2009/0138079 | A1 | 5/2009 | Tuval et al. |
| 2009/0157175 | A1 | 6/2009 | Benichou |
| 2009/0192585 | A1 | 7/2009 | Bloom et al. |
| 2009/0228093 | A1 | 9/2009 | Taylor et al. |
| 2009/0276040 | A1 | 11/2009 | Rowe et al. |
| 2009/0281619 | A1 | 11/2009 | Le et al. |
| 2009/0299456 | A1 | 12/2009 | Melsheimer |
| 2009/0319037 | A1 | 12/2009 | Rowe et al. |
| 2010/0030318 | A1 | 2/2010 | Berra |
| 2010/0036472 | A1 | 2/2010 | Papp |
| 2010/0036473 | A1 | 2/2010 | Roth |
| 2010/0049313 | A1 | 2/2010 | Alon et al. |
| 2010/0076402 | A1 | 3/2010 | Mazzone et al. |
| 2010/0076541 | A1 | 3/2010 | Kumoyama |
| 2010/0082089 | A1 | 4/2010 | Quadri et al. |
| 2010/0094393 | A1* | 4/2010 | Cordeiro .................. A61F 2/95 623/1.11 |
| 2010/0094394 | A1 | 4/2010 | Beach et al. |
| 2010/0121425 | A1 | 5/2010 | Shimada |
| 2010/0145431 | A1 | 6/2010 | Wu et al. |
| 2010/0161036 | A1 | 6/2010 | Pintor et al. |
| 2010/0174363 | A1 | 7/2010 | Castro |
| 2010/0198347 | A1 | 8/2010 | Zakay et al. |
| 2010/0274344 | A1 | 10/2010 | Dusbabek et al. |
| 2011/0015729 | A1 | 1/2011 | Jimenez et al. |
| 2011/0054596 | A1 | 3/2011 | Taylor |

(56) References Cited

U.S. PATENT DOCUMENTS

| | | | | |
|---|---|---|---|---|
| 2011/0137331 | A1 | 6/2011 | Walsh et al. | |
| 2011/0160846 | A1 | 6/2011 | Bishop et al. | |
| 2011/0251681 | A1 | 10/2011 | Shipley et al. | |
| 2012/0123529 | A1 | 5/2012 | Levi et al. | |
| 2012/0239142 | A1 | 9/2012 | Liu et al. | |
| 2013/0013049 | A1* | 1/2013 | Melsheimer | A61F 2/95 623/1.12 |
| 2013/0030519 | A1* | 1/2013 | Tran | A61F 2/958 623/2.11 |
| 2013/0317598 | A1 | 11/2013 | Rowe et al. | |
| 2014/0296962 | A1 | 10/2014 | Cartledge et al. | |
| 2017/0056169 | A1 | 3/2017 | Johnson et al. | |
| 2017/0065415 | A1 | 3/2017 | Rupp et al. | |
| 2018/0153689 | A1 | 6/2018 | Maimon et al. | |
| 2018/0256378 | A1* | 9/2018 | Callister | A61F 2/915 |
| 2018/0344456 | A1 | 12/2018 | Barash et al. | |
| 2019/0070002 | A1 | 3/2019 | Fitterer et al. | |
| 2019/0269890 | A1* | 9/2019 | Bierman | A61M 25/0668 |
| 2020/0108236 | A1* | 4/2020 | Salazar | A61M 25/0662 |
| 2020/0238056 | A1* | 7/2020 | Fantuzzi | A61M 25/1002 |

FOREIGN PATENT DOCUMENTS

| | | | |
|---|---|---|---|
| DE | 19907646 | A1 | 8/2000 |
| EP | 0592410 | B1 | 10/1995 |
| EP | 0850607 | A1 | 7/1998 |
| FR | 2815844 | A1 | 5/2002 |
| JP | 2012183092 | A | 9/2012 |
| JP | 2015513438 | A | 5/2015 |
| WO | 9117720 | A1 | 11/1991 |
| WO | 9829057 | A1 | 7/1998 |
| WO | 9912483 | A1 | 3/1999 |
| WO | 0149213 | A2 | 7/2001 |
| WO | 0154625 | A1 | 8/2001 |
| WO | 0176510 | A2 | 10/2001 |
| WO | 0222054 | | 3/2002 |
| WO | 0236048 | A1 | 5/2002 |
| WO | 0247575 | A2 | 6/2002 |
| WO | 02060352 | | 8/2002 |
| WO | 03030776 | A2 | 4/2003 |
| WO | 03047468 | | 6/2003 |
| WO | 2004019825 | A1 | 3/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2010121076 | A2 | 10/2010 |
| WO | WO-2020123230 | A1 | 6/2020 |

* cited by examiner

FIG. 12A
FIG. 12
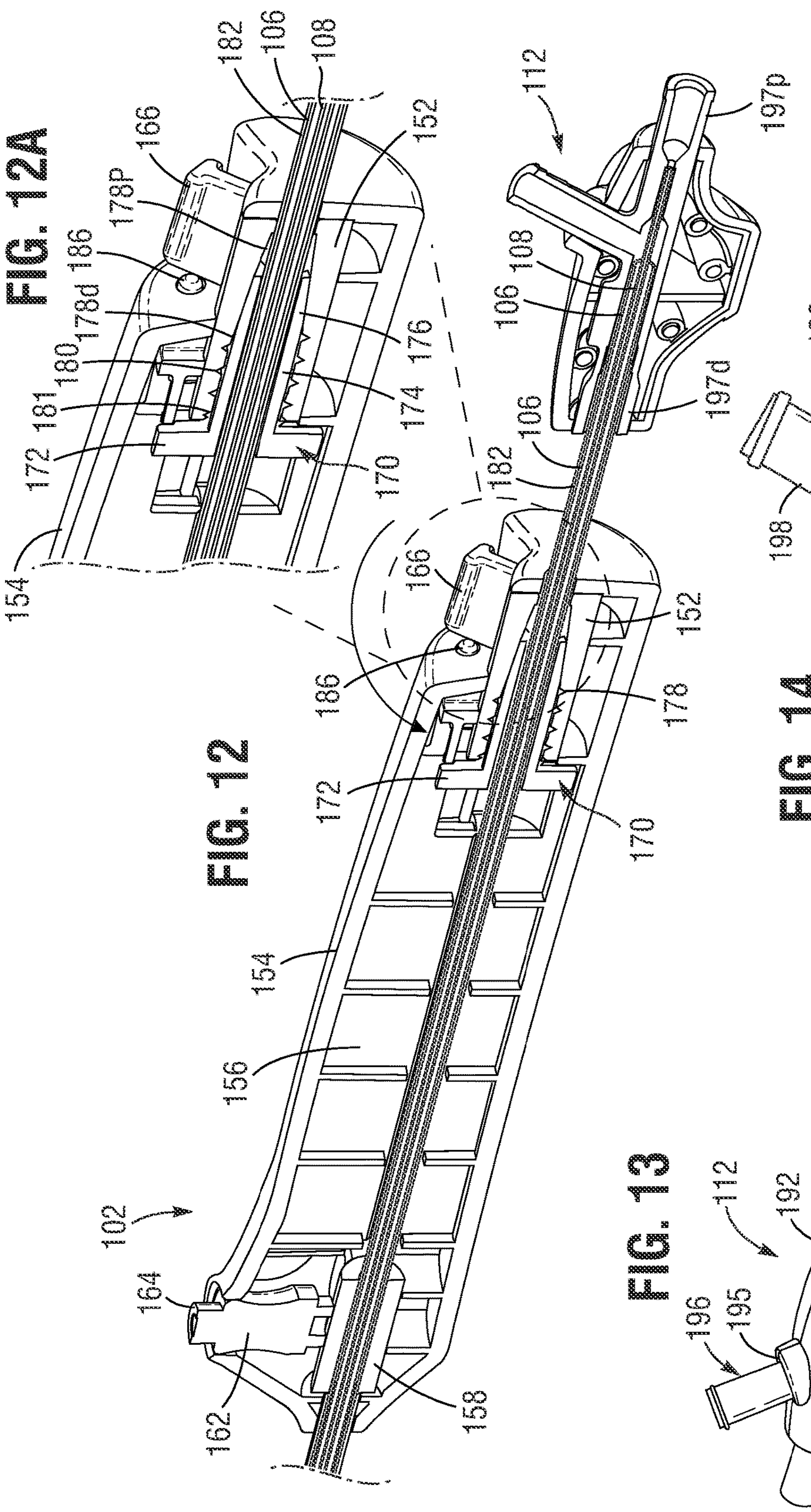
FIG. 14
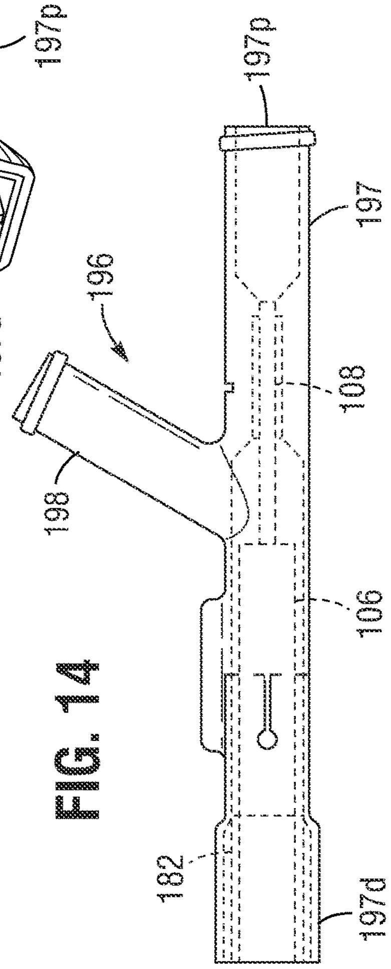
FIG. 13
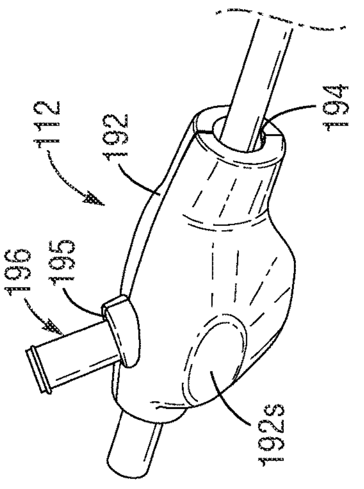

PROSTHETIC VALVE DELIVERY SYSTEM

CROSS-REFERENCE TO RELATED APPLICATION

This application is a continuation of PCT Patent Application No. PCT/US2021/052669, filed on Sep. 29, 2021, which claims the benefit of U.S. Provisional Applications No. 63/085,901, filed Sep. 30, 2020, each of these applications being incorporated herein in their entirety by this specific reference.

FIELD

The present disclosure concerns embodiments of a delivery system for implantation of a prosthetic valve, such as a prosthetic pulmonary valve.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

Transcatheter heart valves may be appropriately sized to be placed inside most native aortic valves. However, with larger native valves, blood vessels, and grafts, aortic transcatheter valves might be too small to secure into the larger implantation or deployment site. In this case, the transcatheter valve may not be large enough to sufficiently expand inside the native valve or other implantation or deployment site to be secured in place.

Replacing the pulmonary valve, which is sometimes referred to as the pulmonic valve, presents significant challenges. The geometry of the pulmonary artery can vary greatly from patient to patient. Typically, the pulmonary artery outflow tract after corrective surgery is too wide to provide adequate support structure for effective placement of a prosthetic heart valve.

One example approach to overcome such challenge is to use a docking device, or docking station, which is configured to be pre-implanted in the target implantation site, and then the prosthetic valve can be deployed within the docking device. The docking device can be configured to compensate for the deployed prosthetic valve being smaller than the annular space in which it is to be placed. However, conventional delivery systems for aortic valve implantation may not be convenient for delivering and implanting a prosthetic valve at the native pulmonary valve. Accordingly, improvements to the transcatheter delivery apparatus are desirable.

SUMMARY

The present disclosure is directed toward methods and apparatuses relating to transvascular implantation of a prosthetic valve, such as a prosthetic pulmonary valve.

Certain embodiments of the disclosure concern delivery apparatus for implanting a prosthetic valve. The delivery apparatus can include a handle, a first shaft extending from a distal end of the handle, a second shaft extending through a lumen of the first shaft and the handle, and a gripper located proximal to a proximal end of the handle. A proximal end of the second shaft can be connected to the gripper, and the gripper can be axially moveable relative to the handle such that axial movement of the gripper causes corresponding axial movement of the second shaft relative to the first shaft. The gripper can have a bottom surface that is substantially coplanar with a bottom surface of the handle.

Certain embodiments of the disclosure also concern another delivery apparatus for implanting a prosthetic valve. The delivery apparatus can include a handle, a first shaft extending from a distal end of the handle, a second shaft extending through a lumen of the first shaft and the handle, and a gripper located proximal to a proximal end of the handle. A proximal end of the second shaft can be connected to the gripper, and the gripper can be axially moveable relative to the handle such that axial movement of the gripper causes corresponding axial movement of the second shaft relative to the first shaft. A distance from a longitudinal axis of second shaft to a bottom surface of the gripper can be substantially identical to a distance from a longitudinal axis of the first shaft to a bottom surface of the handle.

Certain embodiments of the disclosure concern yet another delivery apparatus for implanting a prosthetic valve. The delivery apparatus can include a handle having a locking mechanism, a first shaft extending from a distal end of the handle, and a second shaft extending through the handle. The locking mechanism can include a rotatable locker body having internal threads and a collet at least partially received within the locker body. The collet can include external threads engaging the internal threads of the locker body and be coaxially disposed around the second shaft. Rotation of the locker body can produce axial movement of the collet relative to the locker body and the second shaft. The locker body can be rotatable between a locked position and an unlocked position. When the locker body is in the unlocked position, the second shaft can be axially moveable relative to the handle, the first shaft, and the collet, and when the locker body is in the unlocked position, the collet can prevent axial movement of the second shaft relative to the first shaft and the handle.

Certain embodiments of the disclosure also concern another delivery apparatus for implanting a prosthetic valve. The delivery apparatus can include a handle having a locking mechanism that includes a locker body having a user-engageable portion, a first shaft extending from a distal end of the handle, and a second shaft extending through the handle. The locker body can be moveable between a locked position and an unlocked position. When the locker body is in the unlocked position, the second shaft can be axially moveable relative to the handle and the first shaft. When the locker body is in the unlocked position, the second shaft cannot be axially movable relative to the first shaft and the handle. The delivery apparatus can further include at least one detent element positioned to engage the user-engageable portion when the locker body is in the locked position or the unlocked position.

Certain embodiments of the disclosure further concern another delivery apparatus. The delivery apparatus can include a handle having a chamber and a stopper disposed inside the chamber, a first shaft extending from a distal end of the handle, a gripper located proximal to a proximal end of the handle, and a second shaft extending through the handle and an opening on the stopper. A proximal end of the second shaft can be connected to the gripper. The gripper can be configured to be axially moveable relative to the handle such that axial movement of the gripper causes corresponding axial movement of the second shaft relative to the first shaft and the handle. The second shaft can include a flared portion. The flared portion can have a diameter that is larger than a diameter of the opening on the stopper such that proximal movement of the second shaft is blocked when the flared portion abuts the stopper.

Certain embodiments of the disclosure also concern a method for implanting a prosthetic valve. The method can include inserting a delivery apparatus into a vasculature of a patient, the delivery apparatus including a handle, a first shaft extending from a distal end of the handle, and a second shaft extending through a lumen of the first shaft and the handle. The prosthetic valve can be crimped over a non-inflated balloon coupled to a distal end portion of the second shaft, and the prosthetic valve can be covered by a valve sheath connected to a distal end portion of the first shaft. A proximal end of the second shaft can be connected to a gripper located proximal to a proximal end of the handle. A distance from an axial axis of second shaft to a bottom surface of the gripper can be substantially identical to a distance from an axial axis of the first shaft to a bottom surface of the handle.

Certain embodiments of the disclosure further concern an assembly including a radially expandable and compressible prosthetic valve, and a delivery apparatus including a handle, a gripper located proximal to a proximal end of the handle, a first shaft extending from a distal end of the handle, and a second shaft extending through a lumen of the first shaft and the handle. A proximal end of the second shaft can be connected to the gripper. The prosthetic valve can be mounted over an inflatable balloon coupled to a distal end portion of the second shaft. The handle can include a locking mechanism. The locking mechanism can include a locker body having a user-engageable portion. The locker body can be moveable between a locked position and an unlocked position. When the locker body is in the unlocked position, the gripper can be axially moveable relative to the handle, and when the locker body is in the unlocked position, the gripper cannot be axially movable relative to the handle. The user-engagement portion can be configured to engage at least one detent element when the locker body is in the locked position or unlocked position.

The foregoing and other objects, features, and advantages of the disclosed technology will become more apparent from the following detailed description, which proceeds with reference to the accompanying figures.

BRIEF DESCRIPTION OF THE DRAWINGS

FIG. 12 is a side cross-sectional view of the handle and gripper depicted in FIG. 10A.

FIG. 12A is an enlarged view of a portion of the handle depicted in FIG. 12.

FIG. 13 is a perspective view of the gripper depicted in FIG. 10A.

FIG. 14 is a side elevation view of a Y-connector integrated with the gripper depicted in FIG. 10A.

DETAILED DESCRIPTION

Figure 1:
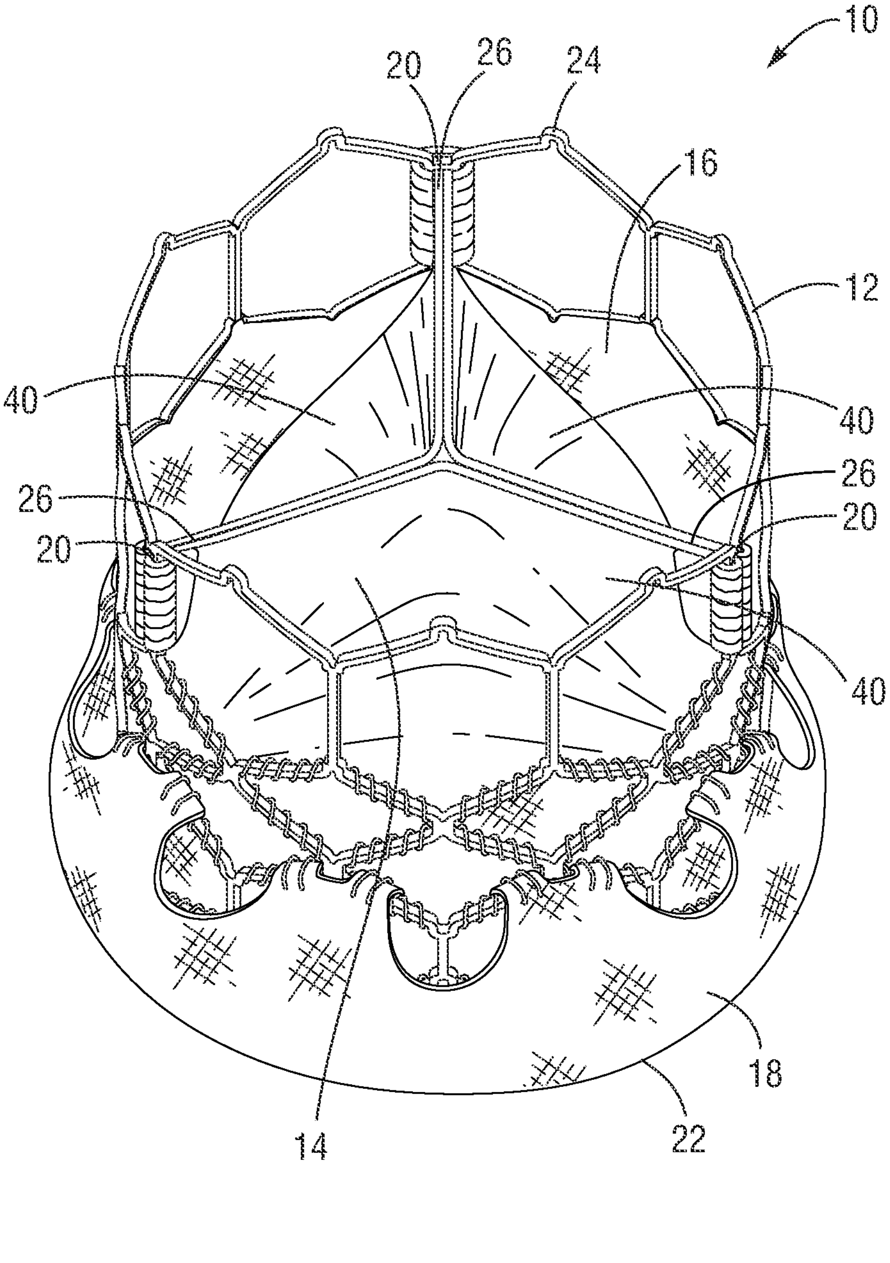
FIG. 1 is a perspective view of a prosthetic heart valve, according to one embodiment.

FIG. 1 shows perspective view of a prosthetic heart valve 10, according to one embodiment. The illustrated valve can be adapted to be implanted in the native pulmonary valve annulus, although in other embodiments it can be adapted to be implanted in the other native annuluses of the heart, such as the native aortic annulus. The valve 10 can have four main components: a stent, or frame, 12, a valvular structure 14, an inner skirt 16, and an outer skirt 18.

The valvular structure 14 can comprise three leaflets 40, collectively forming a leaflet structure (although a greater or fewer number of leaflets can be used), which can be arranged to collapse in a tricuspid arrangement. The leaflets 40 are configured to permit the flow of blood from an inflow end 22 to an outflow end 24 of the prosthetic valve 10 and block the flow of blood from the outflow end 24 to the inflow end 22 of the prosthetic valve 10. The leaflets 40 can be secured to one another at their adjacent sides to form commissures 26 of the leaflet structure. The lower edge of leaflet structure 14 desirably has an undulating, curved scalloped shape. By forming the leaflets with this scalloped geometry, stresses on the leaflets can be reduced, which in turn can improve durability of the valve. Moreover, by virtue of the scalloped shape, folds and ripples at the belly of each leaflet (the central region of each leaflet), which can cause early calcification in those areas, can be eliminated or at least minimized. The scalloped geometry can also reduce the amount of tissue material used to form leaflet structure, thereby allowing a smaller, more even crimped profile at the inflow end of the valve. The leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The frame 12 can be formed with a plurality of circumferentially spaced slots, or commissure windows 20 (three in the illustrated embodiment) that are adapted to mount the commissures 26 of the valvular structure 14 to the frame. The frame 12 can be made of any of various suitable plastically-expandable materials (e.g., stainless steel, etc.) or self-expanding materials (e.g., Nitinol) as known in the art. When constructed of a plastically-expandable material, the frame 12 (and thus the valve 10) can be crimped to a radially compressed state on a delivery apparatus and then expanded inside a patient by an inflatable balloon or equivalent expansion mechanism. When constructed of a self-expandable material, the frame 12 (and thus the valve 10) can be crimped to a radially compressed state and restrained in the compressed state by insertion into a sheath or equivalent mechanism of a delivery apparatus. Once inside the body, the valve can be advanced from the delivery sheath, which allows the valve to expand to its functional size.

Suitable plastically-expandable materials that can be used to form the frame 12 include, without limitation, stainless steel, a nickel based alloy (e.g., a cobalt-chromium or a nickel-cobalt-chromium alloy), polymers, or combinations thereof. In particular embodiments, frame 12 is made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight. It has been found that the use of MP35N to form frame 12 can provide superior structural results over stainless steel. In particular, when MP35N is used as the frame material, less material is needed to achieve the same or better performance in radial and crush force resistance, fatigue resistances, and corrosion resistance. Moreover, since less material is required, the crimped profile of the frame can be reduced, thereby providing a lower profile valve assembly for percutaneous delivery to the treatment location in the body.

The inner skirt 16 can be secured to the inside of frame 12 via sutures. In some embodiments, valvular structure 14 can be attached to the inner skirt 16 via one or more thin polyethylene terephthalate (PET) reinforcing strips, which enables a secure suturing and protects the pericardial tissue of the leaflet structure from tears. The inner skirt 16 can assist in securing the valvular structure 14 to the frame 12 and to assist in forming a good seal between the valve and the native annulus by blocking the flow of blood through the open cells of the frame 12 below the lower edge of the leaflets. The inner skirt 16 desirably comprises a tough, tear resistant material such as PET, although various other synthetic or natural materials can be used. The thickness of the inner skirt desirably is less than 6 mil, and desirably less than 4 mil, and even more desirably about 2 mil. In particular embodiments, the inner skirt 16 can have a variable thickness, for example, the skirt can be thicker at its edges than at its center. In one implementation, the inner skirt 16 can comprise a PET skirt having a thickness of about 0.07 mm at its edges and about 0.06 mm at its center. The thinner inner skirt can provide for better crimping performances while still providing good perivalvular sealing.

The outer skirt 18 can be laser cut or otherwise formed from a strong, durable piece of material, such as woven PET, although other synthetic or natural materials can be used. The outer skirt 18 can be secured to the outside of the frame 12 via sutures. The outer skirt 18 can be so configured that when the frame is in its expanded state, there is excess material or slack between the skirt's lower and upper edges that does not lie flat against the outer surface of the frame 12. The slack between the lower and upper edges of the outer skirt 18 allows the frame 12 to elongate axially when crimped without any resistance from the outer skirt. Also, when the valve 10 is deployed within the body, the excess material of the outer skirt 18 can fill in gaps between the frame 12 and the surrounding native annulus to assist in forming a good fluid-tight seal between the valve and the native annulus. When implanted in an outer docking stent (as described below), the outer skirt 18 can seal against the inner surface of the docking stent. The outer skirt 18 therefore can cooperate with the inner skirt 16 to avoid perivalvular leakage after implantation of the valve 10.

Further details of the valve 10 and its components are described in U.S. Pat. No. 9,393,110, which is incorporated herein by reference.

Figure 2:
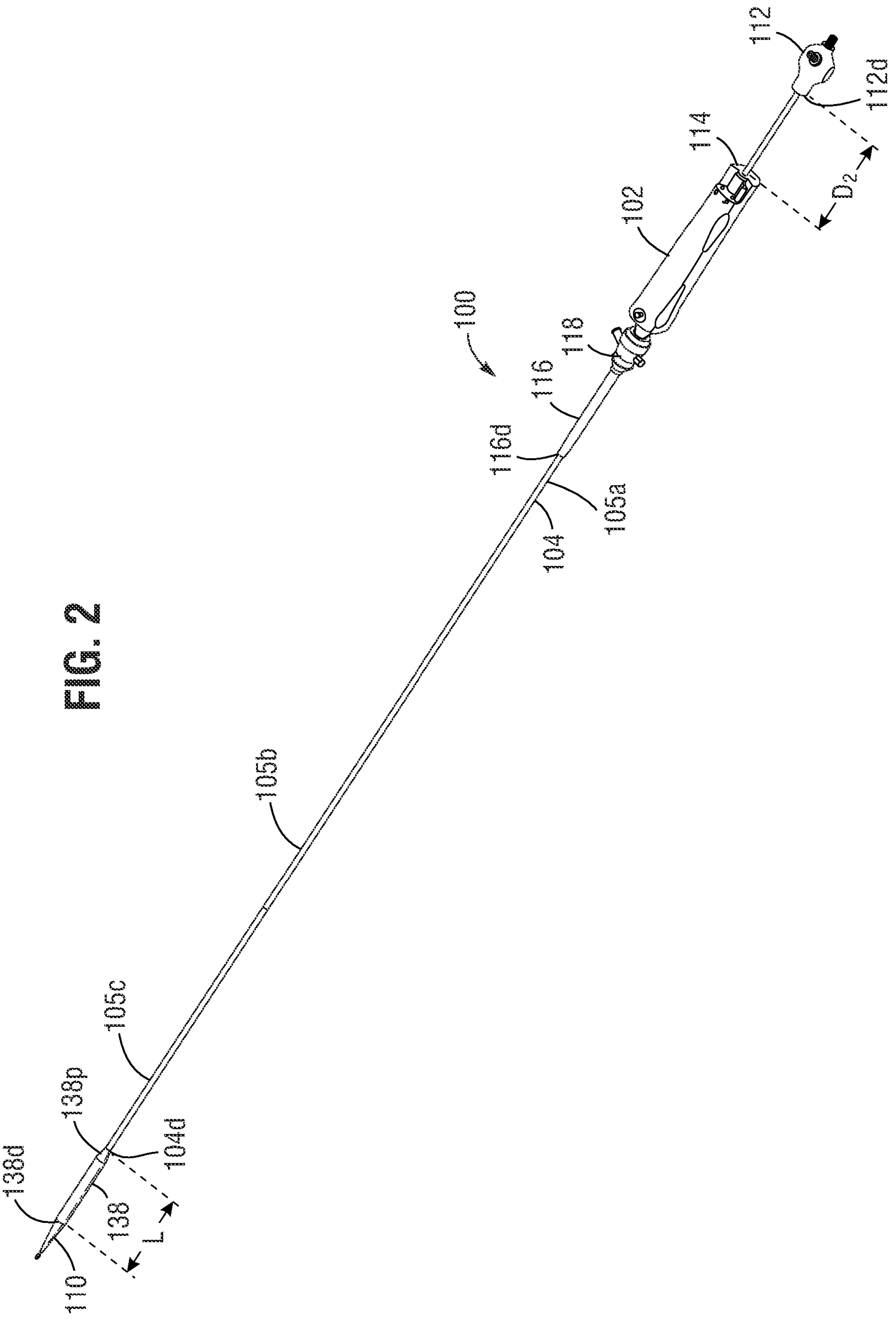
FIG. 2 is a perspective view of a delivery apparatus, according to one embodiment, with a valve sheath shown in a distal position covering a distal end portion of a balloon catheter.
Figures 3, 3A, 3B:
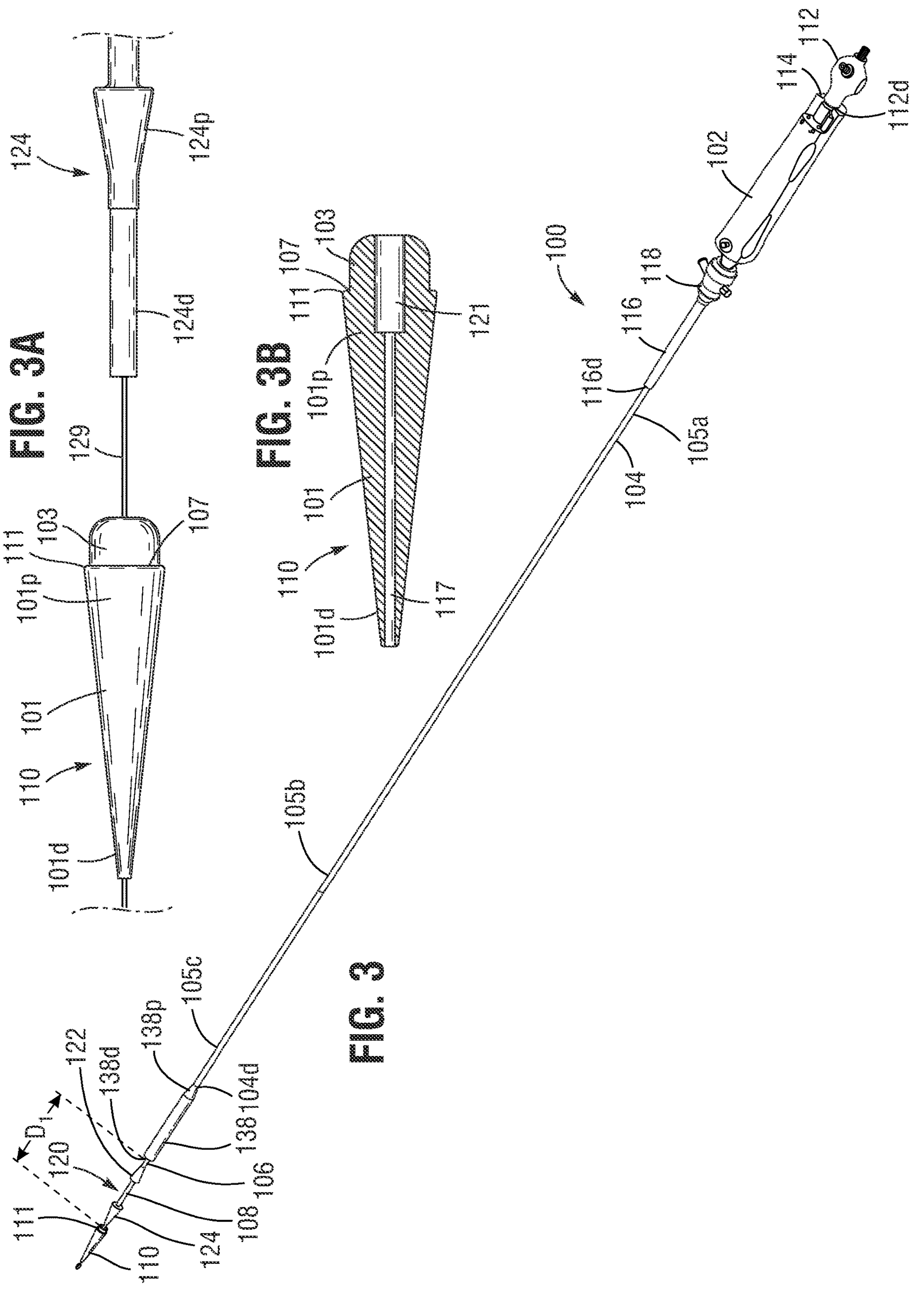
FIG. 3 is a perspective view of the delivery apparatus depicted in FIG. 2, with the valve sheath shown in a proximal position uncovering the distal end portion of the balloon catheter.
FIG. 3A is a side elevation view of a nose cone and a distal shoulder of the delivery apparatus of FIG. 3.
FIG. 3B is a side cross-sectional view of the nosecone of FIG. 3A.

FIGS. 2-3 show a delivery apparatus 100, which can be used to implant a prosthetic valve (such as the prosthetic valve 10) at a target implantation side of a patient, such as the native pulmonary annulus, according to one embodiment. In particular embodiments, the delivery apparatus 100 can be used to implant a prosthetic valve within a docking stent implanted in the native pulmonary annulus or the pulmonary artery, as described in detail below.

As shown, the delivery apparatus 100 can include a handle 102, a first shaft 104 (which is an outer shaft in the illustrated embodiment) extending from a distal end of the handle 102, and a second shaft 106 (which is an intermediate shaft in the illustrated embodiment) extending through a lumen of the first shaft 104 and the handle 102. The second shaft can also be referred to as a "balloon shaft" because an inflatable balloon is mounted on a distal end portion of the second shaft, as described in further detail below. The delivery apparatus 100 can also include a third shaft 108 (which is an inner shaft in the illustrated embodiment) extending through a lumen of the second shaft 106. A distal end of the third shaft 108 can be connected to a nosecone 110, which can have a tapered distal end portion for atraumatic navigation through the patient's vasculature. In some embodiments, a guidewire (not shown) can extend through a lumen of the third shaft 108 and the nosecone 110 so that the delivery apparatus 100 can navigate through the patient's vasculature over the previously inserted guidewire.

As shown, the delivery apparatus 100 includes a gripper 112 located proximal to a proximal end 114 of the handle 102. As described more fully below, a proximal end of the balloon shaft 106 can be connected to the gripper 112 such that axial movement of the gripper 112 relative to the handle 102 can cause corresponding axial movement of the balloon shaft 106 relative to the outer shaft 104 (and the handle 102). Similarly, a proximal end of the inner shaft 108 can also be connected to the gripper 112 such that axial movement of the of the gripper 112 relative to the handle 102 can cause corresponding axial movement of the inner shaft 108 relative to the outer shaft 104 (and the handle). Thus, in the illustrated embodiment, axial movement of the gripper 112 relative to the handle 102 moves the inner shaft 108 and the balloon shaft 106 together relative to the handle 102 and the outer shaft 104.

Figure 4A:
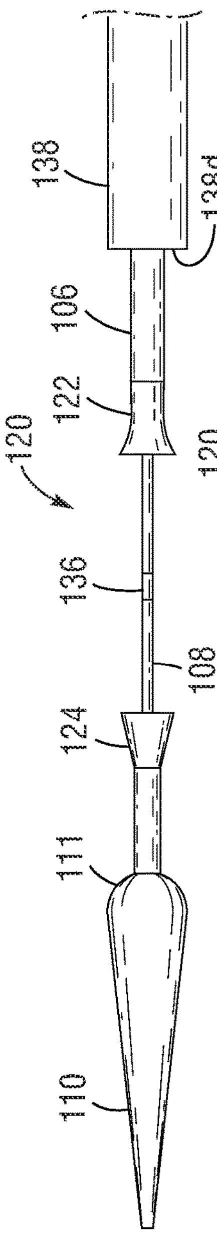
FIG. 4A is a side elevation view of the distal end portion of the balloon catheter depicted in FIG. 3.
Figure 4B:
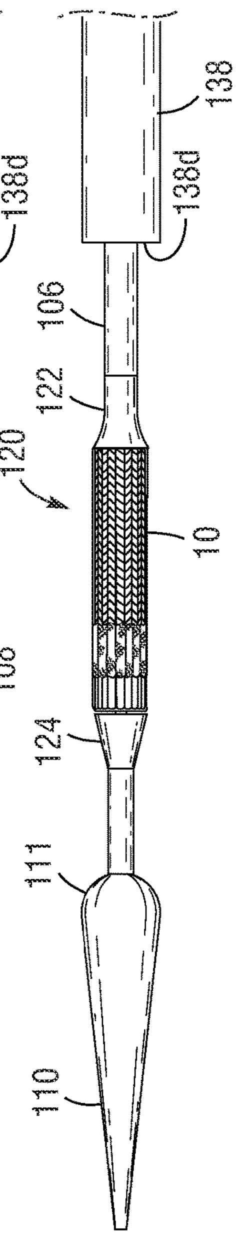
FIG. 4B is a side elevation view of a prosthetic valve mounted on the distal end portion of the balloon catheter depicted in FIG. 3.

As shown in FIG. 3 and FIGS. 4A-4B, a distal end portion of the delivery apparatus 100 can have a balloon shoulder assembly 120 configured to mount an inflatable balloon thereto as described below. The balloon shoulder assembly 120 includes a proximal shoulder 122 connected to a distal end portion of the balloon shaft 106 and a distal shoulder 124 connected to a distal end portion of the inner shaft 108. The proximal shoulder 122 and the distal shoulder 124 are spaced apart from one another, in an axial direction relative to a central longitudinal axis of the delivery apparatus 100.

In some embodiments, the proximal shoulder 122 can be affixed to the distal end portion of the balloon shaft 106 using any known means, such as by welding, an adhesive, mechanical fasteners, etc. Likewise, the distal shoulder 124 can be affixed to the distal end portion of the inner shaft 108 using any known means, such as by welding, an adhesive, mechanical fasteners, etc.

The distal shoulder 124 can have a distal leg portion **124*d* and a proximal flared portion 124*p* that has a larger diameter than the distal leg portion 124*d* (see, e.g., FIG. 3**A).

Similarly, the proximal shoulder 122 can have a proximal leg portion and a distal flared portion that has a larger diameter than the proximal leg portion.

In certain examples, the distal leg portion **124*d* and the proximal flared portion 124*p* of the distal shoulder 124 can be formed as a unitary piece molded from a thermoplastic elastomers, such as Pebax. The distal shoulder 124 can have a durometer ranging from about 35D to about 75D. In one particular example, the distal shoulder 124 has a durometer of about 55D. Similarly, the proximal leg portion and the distal flared portion of the proximal shoulder 122 can be formed as a unitary piece molded from the same or similar materials as the distal shoulder 124. In other examples, the distal leg portion 124*d* and the proximal flared portion 124*p* of the distal shoulder 124 (and/or the proximal leg portion and the distal flared portion of the proximal shoulder 122**) can be initially formed as separated pieces and then bonded together.

In some embodiments, the nosecone 110 and the distal shoulder 124 can be a one-piece or unitary component, that is, the nosecone 110 is a distal portion of the unitary component and the distal shoulder 124 is a proximal portion of the unitary component. In other embodiments, the nosecone 110 and the distal shoulder 124 can be separate components, and each can be mounted on the inner shaft 108 next to each other or at axially spaced locations.

FIGS. 3A-3B further depict the nosecone 110, according to certain examples. As shown, the nosecone 110 can have a body portion 101 and an interface portion 103 extending proximally from the body portion 101. The body portion 101 can have a tapered shape with a progressively decreasing diameter from a proximal end portion **101*p* of the body portion 101 to a distal tip portion 101*d* of the body portion 101. The body portion 101, including its distal tip portion 101*d*, can comprise a flexible material so that the distal tip portion 101*d*** can flex during insertion of the delivery apparatus and/or tracking of the patient's vasculature in the implantation procedure.

The proximal end portion **101*p* of the body portion 101 can have an engagement end 111 configured to engage with a distal end of a valve sheath (e.g., 138), as described further below. The outer diameter at the engagement end 111 can define the largest outer diameter of the nosecone 110. As shown in FIGS. 3A-3B, the interface portion 103 can have a generally cylindrical shape and have an outer diameter that is smaller than the outer diameter at the engagement end 111. Thus, there can be a step decrease of diameter from the proximal end of the body portion 101 to the interface portion 103, forming a vertical wall 107 that is substantially perpendicular to the central longitudinal axis of the delivery apparatus 100. In other examples, the interface portion 103** can have a partially spherical shape.

As described below, a valve sheath (e.g., 138) can be in a covered position (see, e.g., FIG. 2) to cover a radially compressed prosthetic valve (e.g., 10) folded around the balloon shoulder assembly 120. In the covered position, the engagement end 111 of the nosecone 110 can abut a distal end of the valve sheath. As a result, when the distal tip portion **101*d* of the nosecone 110 flexes during the insertion and/or tracking procedures, the distal end of the valve sheath can remain contact with the vertical wall 107 of the nosecone 110 (i.e., preventing axial separation and/or gap between the engagement end 111 of the nosecone 110** and the distal end of the valve sheath).

In some examples, the outer diameter of the interface portion 103 can be about the same as or slightly smaller than an inner diameter of a valve sheath so that a distal end portion of the valve sheath can frictionally engage an outer surface of the interface portion 103. In addition, the outer diameter at the engagement end 111 can be about the same as an outer diameter of the valve sheath. In other words, the height of the vertical wall 107 (i.e., the difference between the outer diameter at the engagement end 111 and the outer diameter of the interface portion 103) can be about the same as the thickness of the valve sheath (i.e., the difference between the outer diameter and inner diameter of the valve sheath). Thus, when the valve sheath is in the covered position, the outer surface of the valve sheath and the outer surface of the body portion 101 of the nosecone 110 can form a continuous smooth surface (i.e., no step increase or decrease of outer diameter).

As depicted in FIGS. 3A-3B, the nosecone 110 can have an inner lumen 117 configured to receive a guidewire 129 and a proximal recess 121 configured to receive the distal leg portion 124*d* of the distal shoulder 124. FIG. 3A shows an exploded view of the nosecone 110 and the distal shoulder 124. The diameter of the proximal recess 121 can be larger than the diameter of the inner lumen 117. The proximal recess 121 can extend from a proximal end of the interface portion 103 into the body portion 101. The inner lumen 117 can extend from a distal end of the proximal recess 121 to a distal end of the body portion 101. During assembly, the distal leg portion 124*d* can be inserted into the recess 121. The distal leg portion 124*d* can be bonded to the nosecone 110, such as with induction welding, an adhesive, etc. The nosecone 110 can be made of the same material as the distal shoulder 124. In some examples, the nosecone 110 and the distal shoulder 124 are made of Pebax, such as Pebax having a durometer of about 55 D.

Figure 5:
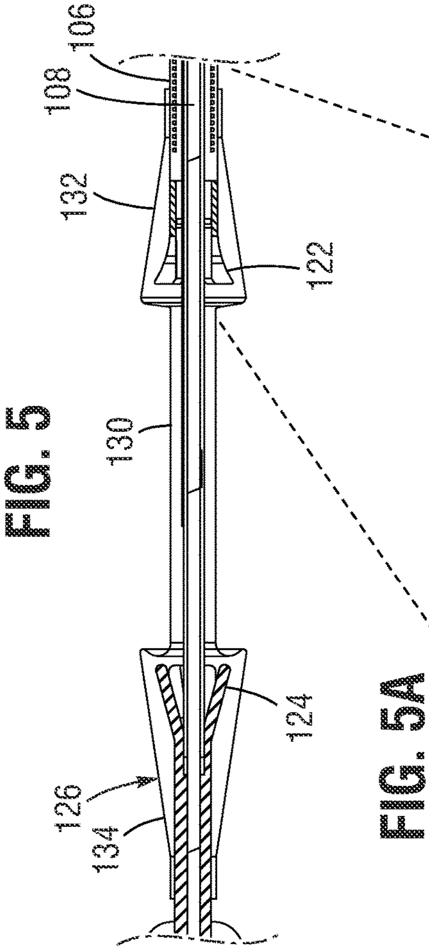
FIG. 5 is a side cross-sectional view of the distal end portion of the balloon catheter depicted in FIG. 3 and a balloon mounted thereto.
Figure 5A:
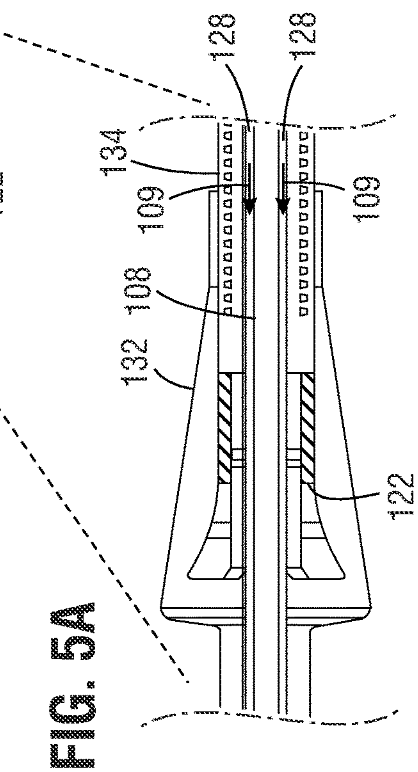
FIG. 5A is an enlarged view of a proximal shoulder portion of the balloon catheter depicted in FIG. 5.

FIG. 5 and FIG. 5A show a cross-sectional view of the balloon shoulder assembly 120 and an inflatable balloon 126 folded around the proximal and distal shoulders. The balloon 126 has a proximal end portion 132 surrounding and/or folded over the proximal shoulder 122 and a distal end portion 134 surrounding and/or folded over the distal shoulder 124. The balloon 126 also has a valve-retaining portion 130 between the proximal end portion 132 and the distal end portion 134, surrounding and/or folded in the space that separates the proximal shoulder 122 and the distal shoulder 124 (e.g., between flared ends of the proximal shoulder 122 and the distal shoulder 124).

As illustrated in FIG. 4B, the prosthetic heart valve 10 can be crimped onto the valve retaining portion 128 of the balloon 126 between the proximal and distal shoulders, which prevent or reduce axial movement of the prosthetic valve 10 relative to the balloon 126 during insertion of the delivery apparatus 100 into the patient's vasculature and delivery of the prosthetic valve 10 to the target implantation site.

As shown in FIG. 5 and FIG. 5A, the outer diameter of the inner shaft 108 can be sized such that an annular space 128 is defined between the inner shaft 108 and the balloon shaft 106 along the entire length of the balloon shaft 106. The annular space 128 can be fluidly coupled to one or more fluid passageways of the delivery apparatus 100 which can be fluidly connectable to a fluid source (e.g., a syringe) that can inject an inflation fluid (e.g., saline) into the delivery apparatus. In this way, fluid from the fluid source can flow through the one or more fluid passageways, through the annular space 128, and into the balloon 126 to inflate the balloon 126 and expand and deploy the prosthetic valve 10. FIG. 5 illustrates the flow of fluid (indicated by arrows 109) through the annular space 128 and through passages in the proximal shoulder 122 and distal shoulder 124. The fluid can then flow into the balloon 126 to expand the valve 10.

In some embodiments, a radiopaque marker 136 can be placed between the proximal shoulder 122 and the distal shoulder 124. For example, the radiopaque marker 136 can be placed on the outer surface of the inner shaft 108 and aligned with the center of the valve retaining portion 130 of the balloon 126. As described below, the radiopaque marker 136 can be used for aligning the prosthetic valve 10 with the native valve under fluoroscopy during an implantation procedure. The radiopaque marker 136 can be optional. For example, in certain embodiments, no radiopaque marker is placed between the proximal shoulder 122 and the distal shoulder 124.

Further details regarding the balloon shoulder assembly, methods of mounting the folding the balloon onto the balloon shoulder assembly, and methods of crimping a prosthetic valve onto the valve retaining portion of the balloon are disclosed in U.S. Publication Nos. 2007/0005131, 2009/0281619, 2013/0030519, 2017/0065415, and U.S. Application No. 62/911,861, all of which are incorporated herein by reference.

As shown in FIGS. 2-3, the delivery apparatus 100 can further include a valve sheath 138 (also referred to as a delivery capsule) which is configured to cover the prosthetic valve 10 mounted on the balloon 126 in a radially compressed state. In the depicted embodiment, a proximal end 138*p* of the valve sheath 138 is connected to a distal end 104*d* of the outer shaft 104. In some embodiments, the proximal end 138*p* of the valve sheath 138 can be fixedly coupled to the distal end 104*d* of the outer shaft 104 by any known means, such as welding, an adhesive, etc.

As noted above, both the balloon shaft 106 and the inner shaft 108 can be axially moveable relative to the outer shaft 104. Thus, the valve sheath 138, which is connected to the outer shaft 104, is axially moveable relative to the proximal shoulder 122 connected to the balloon shaft 106 and the distal shoulder connected to the inner shaft 108. Specifically, the valve sheath 138 is moveable between a covered position, as shown in FIG. 2, and an uncovered position, as shown in FIG. 3.

When the valve sheath 138 is in the covered position (FIG. 2), the engagement end 111 of the nosecone 110 can abut a distal end 138*d* of the valve sheath 138. The length (L) of the valve sheath 138 is configured to be slightly longer than the entire length of the balloon shoulder assembly 120 (measured from the proximal end of the proximal shoulder 122 to the distal end of the distal shoulder 124). Thus, when the valve sheath 138 is in the covered position, the balloon 126 folded around the balloon shoulder assembly 120 can be completely covered by the valve sheath 138. Further, the inner diameter of the valve sheath 138 is configured to be slightly larger than the radial diameter of the prosthetic valve 10 when it is crimped onto the valve retaining portion 130 of the balloon 126. Thus, when the valve sheath 138 is in the covered position, the radially compressed prosthetic valve 10 can be retained inside the valve sheath 138. As described below, the prosthetic valve 10 is retained inside the valve sheath 138 when navigating through the patient's vasculature (e.g., through the tricuspid cordae). Thus, the sheath 138 serves to protect the inside of the patient's vasculature against contact with the outer surface of the prosthetic valve 10 as the delivery apparatus and the prosthetic valve are inserted into and advanced through the patient's vasculature to the implantation site.

In the depicted embodiment, the outer diameter of the valve sheath 138 is larger than the outer diameter of the outer shaft 104. For example, the outer diameter of the valve sheath 138 can range between about 8 mm to about 11 mm in some examples, more desirably between about 9 mm and 10 mm in some examples, and even more desirably between about 9.4 mm and 9.6 mm in some examples (e.g., 9.5 mm). The outer diameter of the outer shaft 104 can range between about 3 mm to about 8 mm in some examples, more desirably between about 5 mm and 6 mm in some examples, and even more desirably between about 5.5 mm and 5.7 mm in some examples (e.g., 5.6 mm). In other embodiments, the outer diameter of the valve sheath 138 can be about the same as the outer diameter of the outer shaft 104.

As shown in FIG. 2, the outer diameter of the valve sheath 138 can be about the same as the outer diameter at the engagement end 111 of the nosecone 110. Thus, when the valve sheath 138 is in the covered position, the outer surface of the valve sheath 138 and the outer surface of the nosecone 110 can form a continuous smooth surface, tapering from the valve sheath 138 to the distal end of the nosecone 110. In some embodiments, the outer surfaces of both the valve sheath 138 and the nosecone 110 are coated with a hydrophilic material to facilitate navigation through the patient's vasculature.

When the valve sheath 138 is in the uncovered position (FIG. 3), the distal end 138*d* of the valve sheath 138 is moved to a position that is proximal to the proximal shoulder 122. Thus, the balloon 126 mounted between the shoulders 122, 124 can be exposed (note that the balloon is omitted from FIG. 3 to illustrate the underlying shoulders). Further, if the prosthetic valve 10 is crimped onto the valve retaining portion 130 of the balloon 126, then the prosthetic valve 10 can be exposed when the valve sheath 138 is in the uncovered position, as illustrated in FIG. 4B. In one particular embodiment, when the valve sheath 138 is in the uncovered position (FIG. 3), the axial distance (D1) between the distal end 138*d* of the valve sheath 138 and the engagement end 111 of the nosecone 110 is about the same as the axial length (L) of the valve sheath 138. In other embodiments, the length (L) can be larger than the distance (D1).

In some embodiments, when the valve sheath 138 is in the covered position (FIG. 2), the axial distance (D2) between the proximal end 114 of the handle 102 and a distal end 112*d* of the gripper 112 is about the same as the distance (D1). Thus, when the distance (D1) is about the same as the axial length (L) of the valve sheath 138, the distance (D2) is about the same as length (L). Accordingly, if the prosthetic valve 10 is originally retained within the valve sheath 138, by axially moving the handle 102 relative to the gripper 112 until the proximal end 114 of the handle 102 abuts the distal end 112*d* of the gripper 112, the valve sheath 138 is moved to the uncovered position and the prosthetic valve 10 can be exposed.

In some embodiments, the outer shaft 104 can comprise multiple sections of varying flexibility along its length. For example, the outer shaft 104 can have a proximal section 105*a*, an intermediate section 105*b*, and a distal section 105*c*. The proximal section can have a higher durometer than the intermediate section, and the intermediate section can have a higher durometer than the distal section. In one specific embodiment, the proximal section 105*a* has a durometer of 72D, the intermediate section 105*b* has a durometer of 55D, and the distal section 105*c* has a durometer of 35D. Thus, the higher flexibility of the distal section makes it easier to advance through tortuous vasculature, and the stiffer intermediate and proximal sections allows for improved steering capability and pushability of the delivery apparatus 100. In other embodiments, the outer shaft 104 can comprise any number of sections (e.g., 1, 2, 4, 5, etc.) with varying durometers along its length.

Figure 6:
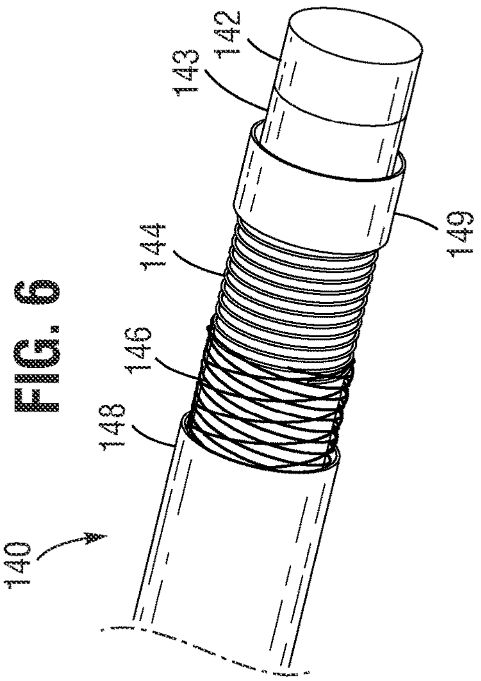
FIG. 6 shows different layers of an outer and the valve sheath of the delivery apparatus, according to one embodiment.
Figure 7:
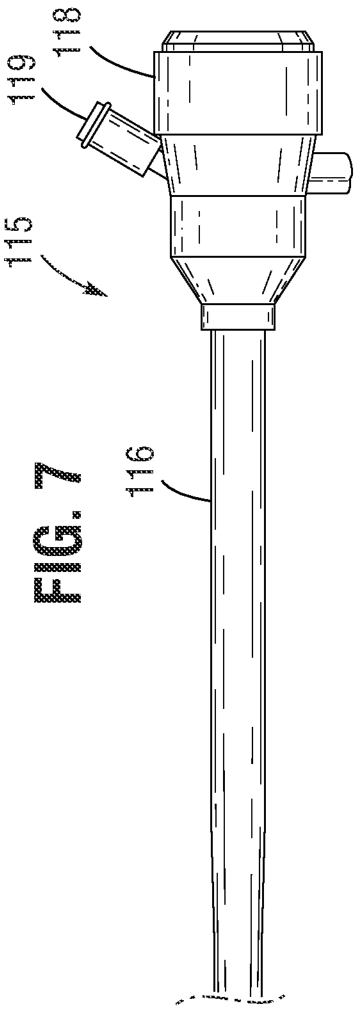
FIG. 7 is a side elevation view of an inline introducer, according to one embodiment.

In some embodiments, the outer shaft 104 (and/or the valve sheath 138) can be constructed using a multi-layer structure to yield desired elasticity and/or rigidity at different sections along its length. For example, FIG. 6 illustrates a tube 140 (which can be a part of the outer shaft 104 and/or the valve sheath 138) having a multi-layer structure, according to one embodiment. In this example, the tube 140 includes an inner liner 142, an optional tie layer 143 extending over the inner liner 142, an optional helical coil member 144 wrapped around the tie layer 143 and the inner liner 142, a braided layer 146 covering the coil member 144, and a heat shrink layer 149 extending over an end of the coil member 144 for the purpose of retention, and an outer layer 148 covering the braided layer 146. The inner liner 142, braided layer 146 and outer layer 148 can extend the full length of the outer shaft 104 and the valve sheath 138, with the valve sheath 138 having a larger outer diameter than the outer shaft 104. In some embodiments, the coil member 144 can extend from the distal end of the valve sheath 138*d* to the proximal end 138*p*. The heat shrink layer 149 can cover a small section of coil member 144 at the distal and proximal ends 138*d*, 138*p* to retain the coil member 144. In certain embodiments, the tie layer 143 can extend from the distal end of the valve sheath 138 to a proximal end of the distal section 105*c* of the outer shaft 104.

In certain embodiments, the inner liner 142 can be made of polytetrafluoroethylene (PTFE), and the tie layer 143 and the outer layer 148 can be made of thermoplastic elastomers, such as Pebax. By applying heat to the heat shrink layer 149 (e.g., a PET material), the heat shrink layer can shrink and apply inward pressure to the coil member 144. Such inward pressure can help retaining coil member 144 at the distal and proximal ends 138*d*, 138*p*. In certain embodiments, the multi-layered shaft 140 can be covered with a disposable heat shrink layer (e.g., fluorinated ethylene propylene, or FEP) and heat can be applied to the entire shaft. The heated outer layer 148 flow into the braided layer 146 and the coil layer 144 to bind those layers together. The multi-layered shaft can then be cooled, after which the disposable heat shrink layer (e.g., FEP) can be removed. By incorporating the helical coil member 144, a section of the tube 140 can be configured to have higher hoop strength and greater anti-kinking ability. On the other hand, a section of the tube 140 can be configured to be more flexible by removing the coil member 144 utilizing outer layers (e.g., Pebax® thermoplastic elastomers) of different durometers. The braided layer 146 also enhances the kink resistance of the shaft. In some embodiments, the braided layer 146 can be configured to have reduced weave density or may be completely removed to further improve the flexibility of the section of the tube 140.

As shown in FIGS. 2-3 and FIGS. 7-8, the delivery apparatus 100 has an integrated inline introducer 115 comprising a sheath 116 and a flush port member 118 (also referred to as a hub) connected to a proximal end of the sheath 116. The outer shaft 104 can be configured to extend through an inner lumen of the sheath 116 and the flush portion member 118. The flush port member 118 can house one or more seals through which the outer shaft 104 extends. The one or more seals can establish a fluid seal against the outer surface of the outer shaft 104. In addition, the delivery apparatus 100 can include a dilator 115 (FIG. 10), which has a tapered tip and is configured to dilate a surgical opening in a blood vessel (e.g., a femoral vein) to facilitate insertion of the distal end portion of the delivery apparatus and the introducer into the blood vessel.

Figure 8:
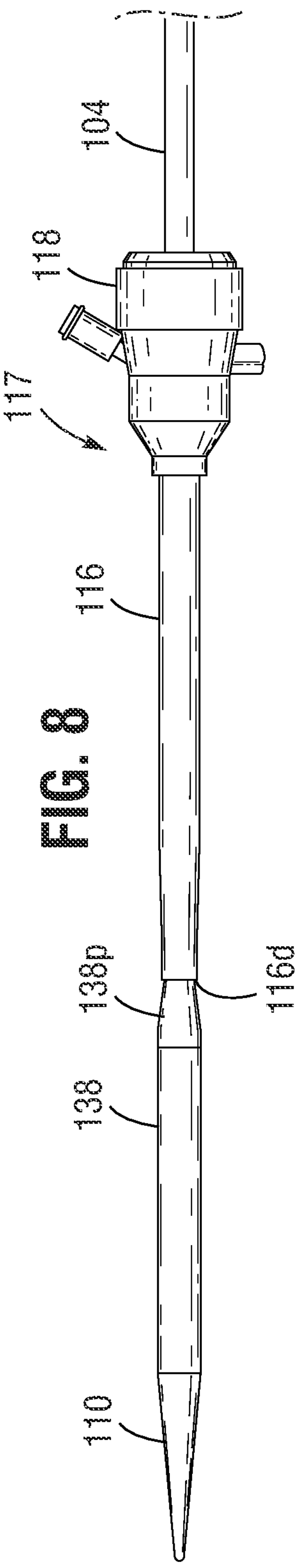
FIG. 8 is a side elevation view of a distal end portion of a delivery apparatus, wherein a proximal end of the valve sheath abuts a distal end of the sheath of the introducer depicted in FIG. 7.
Figure 9:
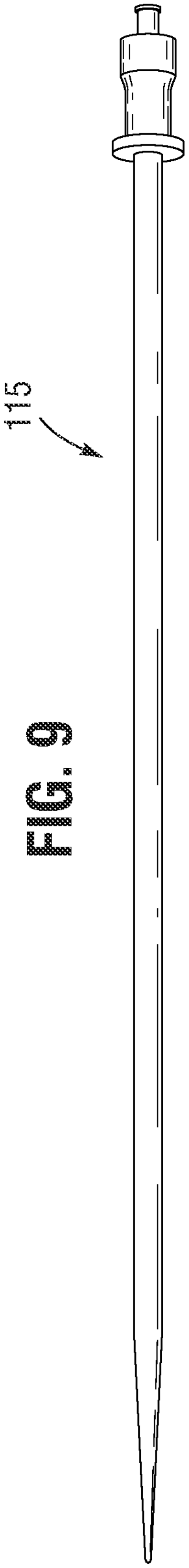
FIG. 9 is a side elevation view of a dilator, according to one embodiment.

The flush portion member 118 can have a flush port 119 through which a fluid, such as saline, may be injected into the introducer so as to flush the inner lumen of the sheath 116 and the outer surface of the outer shaft 114. As best shown in FIG. 8, the outer diameter of the delivery sheath 138 can be greater than the outer diameter of the sheath 116. In some examples, the outer diameter of the sheath 116 can range between about 5 mm to about 12 mm in some examples, more desirably between about 7 mm and 10 mm in some examples, and even more desirably between about 8.2 mm and 8.6 mm in some examples (e.g., 8.4 mm).

Further, the outer shaft 104 and the valve sheath 138 connected thereto are configured to be axially movable relative to the sheath 116 and the flush port member 118. For example, FIGS. 2-3 show that the outer shaft 104 is advanced distally relative to the sheath 116 such that the proximal end 138*p* of the valve sheath 138 is separated from a distal end 116*d* of the sheath 116. On the other hand, FIG. 8 shows that the outer shaft 104 can be moved to a position where the proximal end 138*p* of the valve sheath 138 abuts the distal end 116*d* of the sheath 116.

Figure 10A:
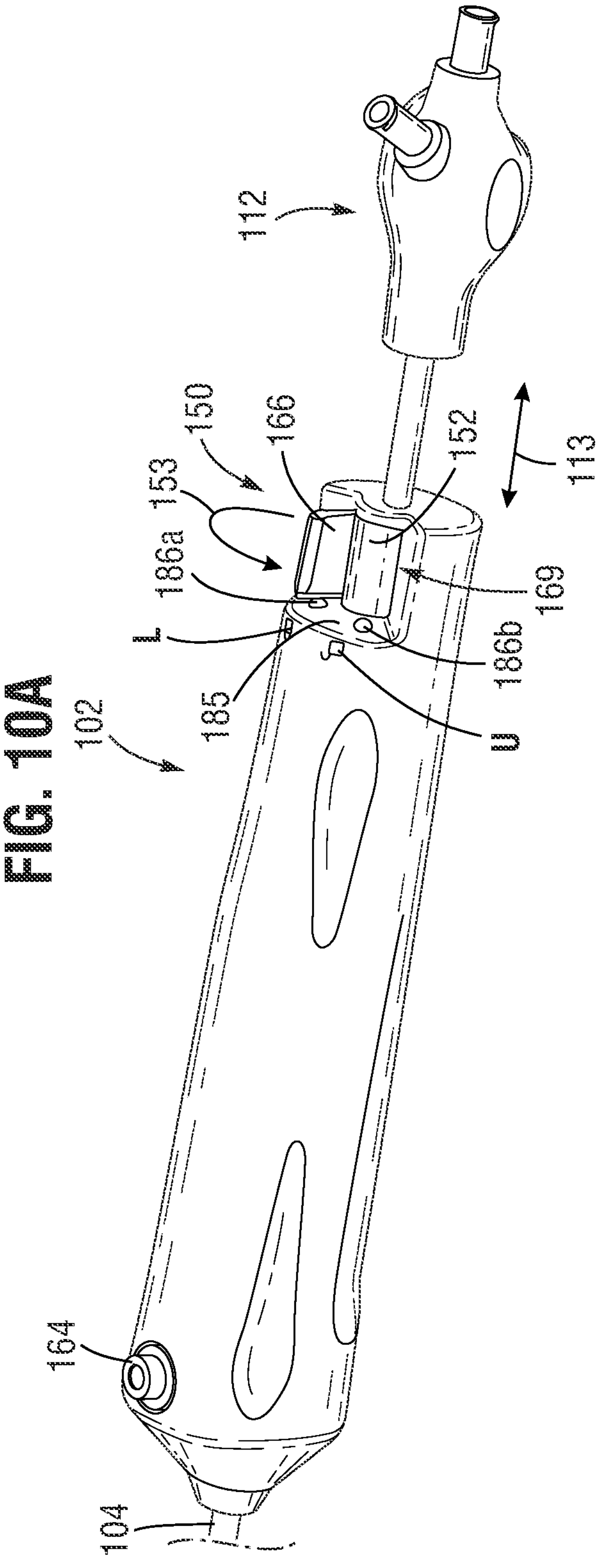
FIG. 10A is a perspective view of a handle and a gripper of the delivery apparatus of FIG. 2.
Figure 10B:
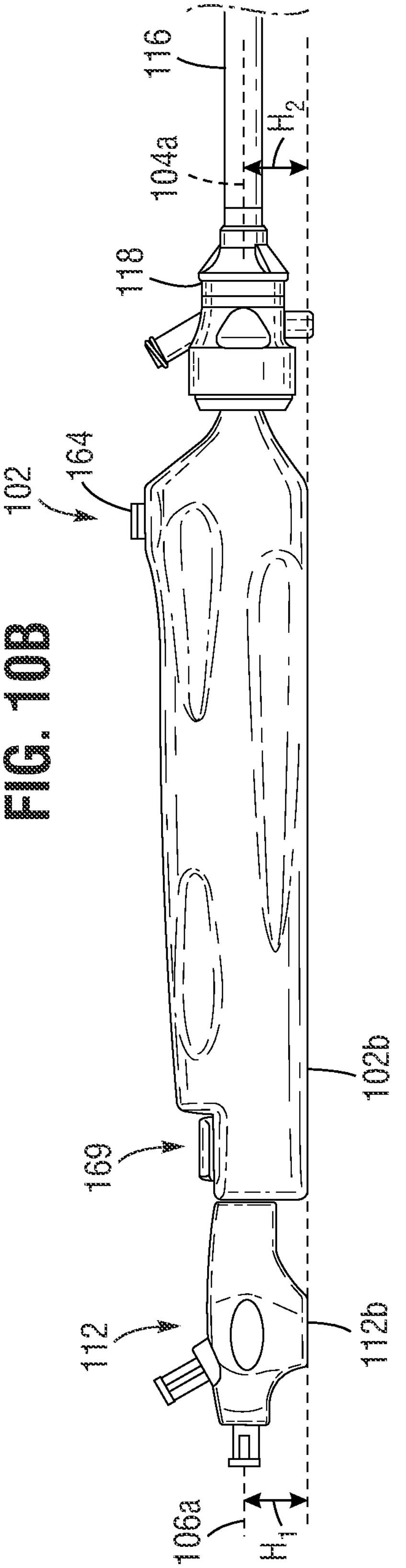
FIG. 10B is a side elevation view of the handle and the gripper depicted in FIG. 10A.
Figure 11:
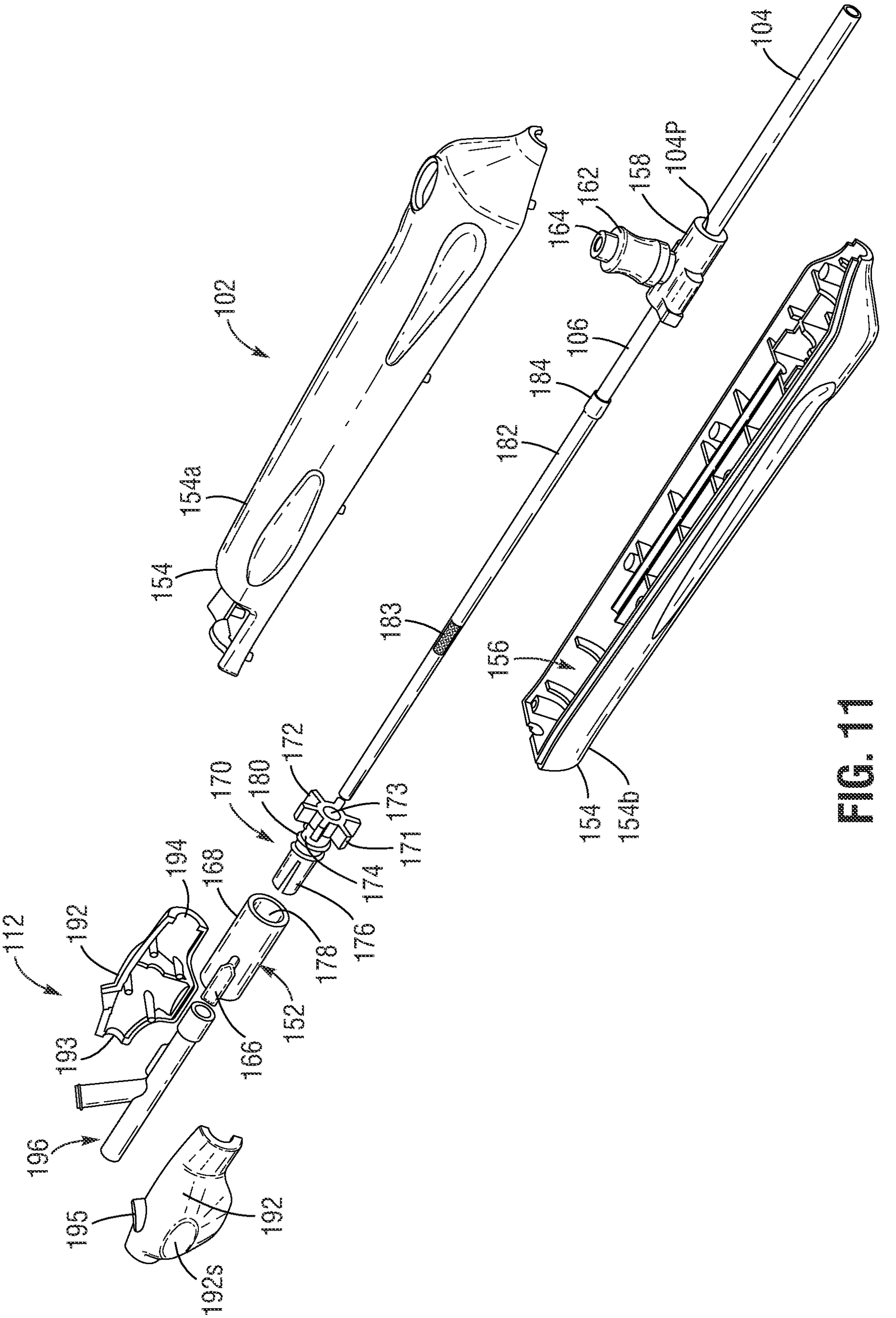
FIG. 11 is an exploded, perspective view of the handle and gripper depicted in FIG. 10A.

FIGS. 10-12 show the handle 102, the gripper 112, and their respective components, according to one embodiment. As described above and indicated by the double-sided arrow 113, the handle 102 and the gripper 112 can be axially moveably relative to each other. Further, the handle 102 can include a locking mechanism 150 which can selectively lock and permit axial movement of the handle 102 relative to the gripper 112. For example, the locking mechanism 150 can include a locker body 152 that is moveable between a locked position (L) and an unlocked position (U) as indicated by arrow 153. As best shown in FIG. 10A, the locked position and the unlocked position can be respectively marked on the handle with visual indicators to an operator of the handle. As described more fully below, the locking mechanism 150 can be configured such that when the locker body 152 is in the unlocked position, the gripper 112 and the shafts connected thereto (e.g., the balloon shaft 106 and the inner shaft 108) are axially moveable relative to the handle 102 and the outer shaft 104. On the other hand, when the locker body 152 is in the locked position, the gripper 112 and the shafts connected thereto (e.g., the balloon shaft 106 and the inner shaft 108) are not axially moveable relative to the handle 102 and the outer shaft 104.

As best shown in FIG. 10B, the gripper 112 has a bottom surface 112*b* that is coplanar or substantially coplanar with a bottom surface 102*b* of the handle 102, according to one example embodiment. The coplanar design of the surfaces 102*b* and 112*b* is advantageous in that it can facilitate linear movement of the handle 102 relative to the gripper 112. For example, in use, a physician can place the handle 102 and the gripper 112 on a surface, such as on an operating table or on the patient's thigh. If the bottom surfaces 102*b* and 112*b* are at different heights, then the shaft section extending between the handle 102 and the gripper 112 (the proximal portions of the balloon shaft 106 and the inner shaft 108) can bend. This in turn can increase friction between the shaft section and the proximal opening of the handle, which can make moving the handle and the gripper relative to each other in an axial direction (proximally and distally) more difficult. By virtue of the surfaces 102*b* and 112*b* being coplanar or substantially coplanar, deflection of the shaft section between the handle and gripper is prevented or minimized when placed on a working surface (e.g., an operating table or the patient's thigh), which reduces the manual pushing and pulling forces required to move these components relative to each other (proximally and distally) and improves control over unsheathing the prosthetic valve 10.

According to one embodiment, the bottom surfaces 112*b* and 102*b* are deemed substantially coplanar when a vertical distance (H1) from a central longitudinal axis 106*a* of the balloon shaft 106 to the bottom surface 112*b* of the gripper 112 is substantially identical to a vertical distance (H2) from a central longitudinal axis 104*a* of the outer shaft 104 to the bottom surface 102*b* of the handle 102. The distances (H1) and (H2) are deemed substantially identical if the difference between (H1) and (H2) is less than 5% of (H2) in certain examples, even more desirably less than 1% of (H2) in certain examples. In a particular embodiment, the central longitudinal axis 106*a* of the balloon shaft 106 coincides with the central longitudinal axis 104*a* of the outer shaft 104 (i.e., the shafts 104 and 106 are coaxial).

The substantial identical heights (H1) and (H2) can ensure that the balloon shaft 106 and the outer shaft 104 remain substantially coaxial when the handle 102 and the gripper 112 are placed on a working surface and these components are moved axially relative to each other. Otherwise, if (H1) is substantially different from (H2), the shaft section between the handle and gripper can bend, which can increase sliding friction between the shafts and increasing resistance to the axial movement.

FIG. 11 is an exploded view of some components of the handle 102 and the gripper 112, according to one embodiment. As shown, the handle 102 has a housing 154, which can include two half shells 154*a*, 154*b*, each of which can have about a generally semi-cylindrical shape. The shell 154*a* can have longitudinal edges that are configured to matingly engage respective longitudinal edges of the shell 154*b* to form a clam shell configuration. The housing 154 can define a lumen 156 through which the balloon shaft 106 extends.

As shown, the handle 102 can have a hub 158 disposed within a distal end portion of the lumen 156. A proximal end 104*p* of the outer shaft 104 can be fixedly coupled to a distal end of the hub 158. The balloon shaft 106 can extend through a lumen of the hub 158 and the lumen of the outer shaft 104. An O-ring (not shown) can be placed on the balloon shaft 106 at the proximal end of the hub 158 or within the hub to seal any gaps between the outer surface of the balloon shaft 106 and the lumen of the hub 158. A one-way valve 162 can be fluidly connected to the lumen of hub 158. The one-way valve 162 can have a port 164 extending outside the housing 154 through an opening on one of the half shells (see FIGS. 10A-10B). Thus, through the port 164, a flushing fluid can be injected through the valve 162 into the lumen of the hub 158 and further into the lumen of the outer shaft 104, thereby flushing the outer surface of the balloon shaft 106.

The locker body 152 of the locking mechanism 150 can be disposed within a proximal end portion of the lumen 156 of the handle 102. The locker body 152 can include a cylindrical portion 168 and a user-engageable tab 166 extending radially outwardly from the cylindrical portion 158. The tab 166 can extend into and is rotationally moveable within a recessed or cutout region 169 located at the proximal end portion of the handle 102 (see FIGS. 10A-10B).

The locking mechanism 150 can further include a collet 170 that is at least partially received within a lumen 178 of the locker body 152. For example, in the embodiment depicted in FIG. 11, the collet 170 includes a star-shaped end plate 172 having a plurality of radial projections 171, a neck portion 174 extending proximally from the end plate 172, and a plurality of cantilevered arms 176 (two are shown in the depicted example) extending proximally from the neck portion 174. As shown in FIG. 12 and FIG. 12A, the arms 176 and neck portion 174 of the collet 170 can be disposed within the lumen 178 of the locker body 152. The lumen 178 has a proximal portion 178*p* and a distal portion 178*d*. The lumen 178 has a tapered shape such that the proximal portion 178*p* has a smaller diameter than the distal portion 178*d*. Each of the projections 171 can abut corresponding interior surface portions of the handle, which allow the collet 170 to slide axially within the handle but prevent rotational movement of the collet relative to the handle.

The delivery apparatus 100 can further include another shaft, such as the illustrated hypotube 182, which can be made of a metal or alloy material and desirably is more rigid and has a higher kink resistance than the balloon shaft 106. As shown in FIGS. 11-12, the hypotube 182 can surround at least a proximal portion of the balloon shaft 106 and extend through the collet 170 and the locker body 152. A proximal end of the hypotube 182 can be connected to the gripper 112. Specifically, the hypotube 182 can extend through an opening 173 in the end plate 172 and a lumen of the neck portion 174, such that the plurality of arms 176 of the collet 170 can be coaxially disposed around the hypotube 182.

The inner surface of the locker body, which defines the lumen 178, can have a plurality of inner threads 181. The neck portion 174 of the collet 170 can have corresponding outer threads 180 that are configured to threadably engage the inner threads 181 of the locker body 152. According to one embodiment, rotating the locker body 152 around its central axis can cause corresponding axial movement of the collet 170 relative to the locker body 152 and the hypotube 182. Movement of the collet 170 can be caused by the threads 180, 181 engaging each other and by the radial projections 171 of the end plate 172 which engage corresponding inner surfaces of the shells 154 so as to prevent rotational movement of the collet 170 but allow it to slide axially. For example, rotating the locker body 152 in a first direction (e.g., toward the locked position) can cause the collet 170 to move in a proximal direction, whereas rotating the locker body 152 in a second direction opposite the first direction (e.g., toward the unlocked position) can cause the collet 170 to move in a distal direction.

According to one embodiment, when the locker body 152 is in the locked position (L), distal end portions of the arms 176 are advanced into the narrower proximal portion 178*p* of the locker lumen 178. As a result, the arms 176 can be resiliently compressed radially inwardly so as to clasp or clamp against the hypotube 182. Because the proximal end of the hypotube 182 is connected to the gripper 112, clamping the hypotube 182 can prevent axial movement between the handle 102 and the gripper 112. When the locker body 152 is in the unlocked position (U), the distal end portions of the arms 176 are moved into the wider distal portion 178*d* of the locker lumen 178. As a result, the resiliently compressed arms 176 can expand radially outwardly, thus releasing their grasp on the hypotube 182, thereby allowing axial movement of the hypotube relative to the collet and axial movement between the gripper 112 and the handle 102.

Figure 15B:
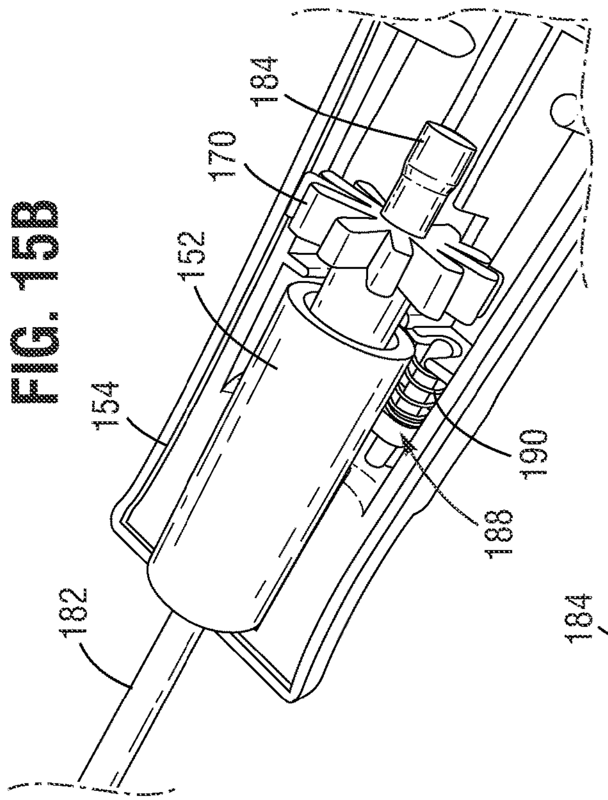
FIG. 15B show components of the locking mechanism depicted in FIG. 15B in an assembled state.
Figure 16:
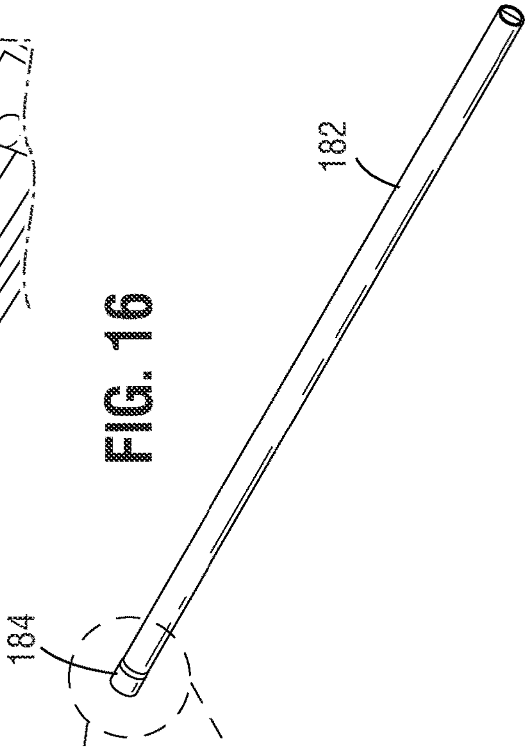
FIG. 16 is a perspective view of a hypotube, according to one embodiment.
Figure 16A:
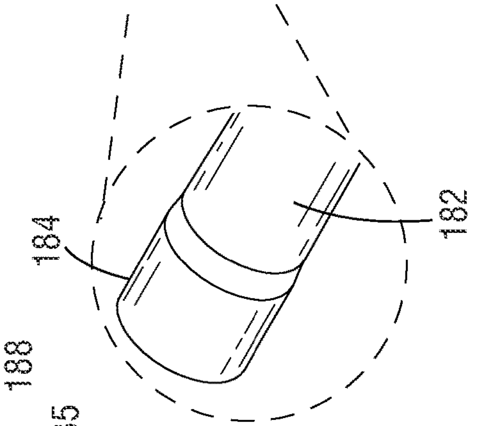
FIG. 16A is an enlarged view of a proximal end of the hypotube depicted in FIG. 16.

As shown in FIG. 16 and FIG. 16A, the hypotube 182 can have a flared distal end portion 184 which has an enlarged diameter relative to the remaining portion of the hypotube. The diameter of the flared portion 184 can be larger than a diameter of the opening 173 in the end plate 172 of the collet 170. Thus, when moving the gripper 112 away from the handle 102 in the proximal direction (and when the locker body 152 is in the unlocked position), the movement of the gripper 112 is prevented when the flared portion 184 abuts the end plate 172 of the collet 170, as best shown in FIG. 15B. In this manner, the end plate 172 can serve as a hard stop for the hypotube 182 to prevent excessive movement of the gripper 112 relative to the handle 102 in the proximal direction.

In the depicted embodiment, the flared portion 184 is located at a distal end of the hypotube 182. In other embodiments, the flared portion 184 can be located at a position that is proximal to the distal end (e.g., at the middle section) of the hypotube 182. The distance between the flared portion 184 and the gripper 112 is selected to determine how far the gripper 112 can be moved axially away from the handle 102 in the proximal direction. In one particular embodiment, the distance between the flared portion 184 and the gripper 112 is equal to or greater than the axial distance (D1) between the distal end 138*d* of the valve sheath 138 and the engagement end 111 of the nosecone 110 when the valve sheath 138 is in the uncovered position (see e.g., FIG. 3). In a specific implementation, the distance between the flared portion 184 and the gripper 112 is about equal to the sum of the distance between the end plate 172 and the proximal end 114 of the handle 102 and the axial distance (D1) between the distal end 138*d* of the valve sheath 138 and the engagement end 111 of the nosecone 110 when the valve sheath 138 is in the uncovered position (see e.g., FIG. 3).

In certain examples, the middle section of the hypotube 182 can have a visually perceivable marker band 183 (see FIG. 11). In certain examples, the marker band 183 can be laser edged on the hypotube 182. In certain examples, the marker band 183 can be painted over the hypotube 182. In certain examples, the marker band 183 can be taped and/or glued on the hypotube 182.

The marker band 183 can be so positioned on the hypotube 182 that the appearance of the marker band 183 in the gap between the gripper 112 and the handle 102 indicates fully capture or resheathing of the balloon 126, as described further below. In other words, when the gripper 112 contacts or is in close proximity to the handle 102 (e.g., the gap between the gripper 112 and handle 102 is smaller than a predetermined distance), at least a portion of the balloon 126 is not covered by the valve sheath 138, and the marker band 183 is hidden by the handle 102 and cannot be observed. When moving the gripper 112 away from the handle 102 in the proximal direction, the gap between the gripper 112 and the handle 102 increases. When the proximal movement of the gripper 112 causes the balloon 126 to be fully covered by the valve sheath 138, the marker band 183 moves out of the handle 102 and can be observed in the gap, providing visual confirmation that the balloon is fully covered by the sheath 138.

In some embodiments, the locking mechanism 150 can further include one or more detent elements 186 in the form of projections protruding from a proximal face 185 that defines the recessed region 169 at the proximal end portion of the handle 102. In the embodiment depicted in FIG. 10A, two such detent elements 186*a*, 186*b* are shown, located between and immediately adjacent to the locked position (L) and unlocked position (U), respectively. The two detent elements 186*a*, 186*b* are angularly spaced apart from each other. The angle between the two detent elements 186*a*, 186*b* can be between about 80° and about 180°, desirably between about 100° and about 160°, and even more desirably between about 120° and about 140° (e.g., about 130°).

The user-engageable tab 166 can be circumferentially turned by an operator to engage and/or disengage the detent elements 186 when moving between the locked position and the unlocked position. Specifically, referring to FIG. 10A, rotating the tab 166 across the first detent element 186*a* in a first angular direction (clockwise in the illustrated embodiment) brings the tab 166 into the locked position and rotating the tab 166 across the second detent element 186*b* in a second angular direction that is opposite the first angular direction (counterclockwise in the illustrated embodiment) brings the tab 166 into the unlocked position.

Figure 15A:
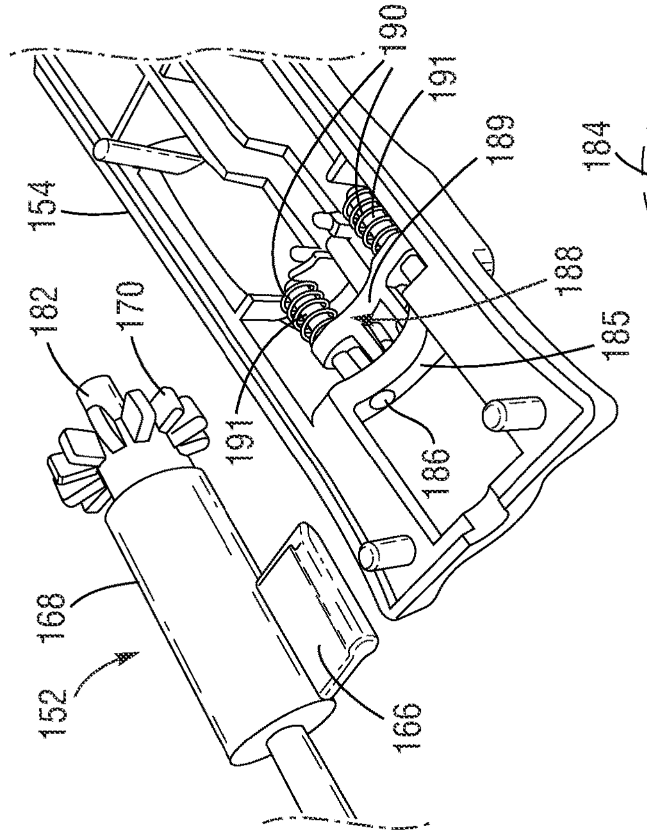
FIG. 15A shows components of a locking mechanism of a handle in a disassembled state, according to one embodiment.

As shown in FIGS. 15A-15B, the detent elements 186 can be parts of a piston 188 that is axially moveable relative to the locker body 152. The two detent elements 186*a* and 186*b* can be connected by a bridge member 187. At least one biasing member can be provided to resiliently urge the detent elements 186*a*, 186*b* to a first position extending further into the recessed region 169 of the handle for engaging the user-engageable tab 166. In the illustrated embodiment, for example, two coiled springs 190 are co-axially disposed on distal projections 191 connected to a distal side of the bridge 189. The proximal ends of the springs 190 bear against the bridge 189 while the distal ends of the springs 190 bear against adjacent surfaces inside the handle 102, thereby biasing the bridge 189 and the detent elements 186*a*, 186*b* in a proximal direction toward the tab 166.

When the user-engageable tab 166 is rotated and passes over one of the detent elements 186*a*, 186*b*, the tab 166 presses against that detent element and moves both detent elements further into the interior handle to a second position against the bias of the springs 190. When the tab 166 is in the locked position, such as shown in FIG. 10A, the detent element 186*a* is in the first position and can engage a side of the tab 166. The biasing force of the springs 190 is selected to prevent inadvertent rotation of the tab 166 away from the locked position until actuated by a user. Similarly, when the tab 166 is in the unlocked position, the detent element 186*b* can engage a side of the tab 166, thereby preventing inadvertent movement of the tab away from the unlocked position until actuated by a user. To move the tab 166 from the unlocked position to the unlocked position, or vice versa, the user applies sufficient manual force to the tab 166 to overcome the bias of the springs 190, which allows the tab to move away from the unlocked position (or the locked position) and pass over the adjacent detent element.

Besides the visual indicators on the handle marking the locked and unlocked positions, the engagement and disengagement between the tab 166 and the detent elements 186 can create additional feedback (e.g., audible clicks and/or tactile vibrations) to the operator to indicate the position of the tab 166.

In some embodiments, the handle 102 can have only one detent element. For example, in one implementation, the handle 102 has only detent element 186*a* for retaining the tab 166 in the locked position. In another implementation, the handle 102 has only detent element 186*b* for retaining the tab 166 in the unlocked position.

In some embodiments, the handle 102 can have respective slots (not shown) that are adjacent to the locked and unlocked positions and located distal to the recessed region 169. The slots can be sized and shaped so as to receive the tab 166 when the tab is in the unlocked or locked positions. Thus, after moving the tab 166 to the locked or unlocked position, the tab 166 can be slid into the respective slot, thereby retaining the tab 166 in place until removed from the slot by the user. In alternative embodiments, other retaining mechanisms (e.g., buckles, clips, hook-and-loop fasteners, etc.) configured to prevent unintentional movement of the tab 166 from the locked or unlocked position can be incorporated into the handle.

As shown in FIGS. 10-13, the gripper 112 can include a body portion or housing 192 and an integrated Y-connector 196 disposed inside the body portion. The body portion 192 can define a lumen through which the Y-connector 196 extends. The body portion 192 can have a proximal opening 193, a distal opening 194, and a side opening 195. In the depicted embodiment, the side opening 195 is located on the top surface of the gripper 112, opposite the bottom surface 112*b*. In other embodiments, the side opening 195 can be located on one of the sidewalls (i.e., between the top and bottom surfaces) of the gripper 112. The body portion 192 can also have two flat or substantially flat side surfaces 192*s* located on opposite sidewalls (one side surface 192*s* is shown in FIG. 13; the other side surface 192*s* is on the opposite of the gripper). In certain examples, the side surfaces 192*s* can be textured (e.g., with grooves) so that the gripper 112 can be easily gripped by two fingers of the operator. In certain examples, the bottom surface 112*b* of the gripper can also be textured (e.g., with grooves) to resist movement when placing the gripper 112 on a flat surface.

In certain examples, the gripper 112 and the balloon shaft 106 can be rotatable about the central longitudinal axis 106*a* of the balloon shaft 106. In certain examples, when the gripper 112 is rotated 90 degrees from the position shown in the drawings (either in clockwise or counter-clockwise direction) such that the side opening 195 points to sideways, one of the side surfaces 192*s* faces downward and can be coplanar or substantially coplanar with the bottom surface 102*b* of the handle 102. This can be achieved, for example, by making the two side surfaces 192*s* and the bottom surface 112*b* equidistant from the axial axis of the gripper (which coincides with the central longitudinal axis 106*a* in FIG. 10B). Thus, the gripper 112 can have three contact surfaces, i.e., the bottom surface 112*b* and the two side surfaces 192*s*, each of which can be placed on an operating table (or other flat surfaces) while ensuring such contact surface is coplanar or substantially coplanar with the bottom surface 102*b* of the handle 102.

As shown in FIG. 14, the Y-connector 196 can have a main tubular portion 197 and a side tubular portion 198 extending angularly from the main tubular portion 197. The main tubular portion 197 can extend through the lumen of the gripper 112 and be substantially parallel to the bottom surface 112*b* of the gripper 112. In the depicted embodiment, a distal end portion 197*d* of the main tubular portion 197 is positioned adjacent the distal end 112*d* of the gripper 112 and a proximal end portion 197*p* of the main tubular portion 197 extends out of the proximal opening 193 of the gripper 112. The side tubular portion 198 can extend through the side opening 195 of the gripper 112.

According to one embodiment, the proximal ends of the balloon shaft 106, the inner shaft 108, and the hypotube 182 are all fixedly coupled to the main tubular portion 197 of the Y-connector 196. In other embodiments, all of the proximal ends of the balloon shaft 106, the inner shaft 108, and the hypotube 182 can be fixedly coupled to the housing 192 of the gripper 112. Yet in alternative embodiments, the proximal end of the hypotube 182 can be fixedly coupled to the body portion 192, the proximal end of the inner shaft 108 can be fixedly coupled to the main tubular portion 197, and the proximal end of the balloon shaft 106 can be fixed coupled to either the body portion 192 or the main tubular portion 197.

The proximal end of the main tubular portion 197 has an opening through which a guidewire can be inserted into a lumen of the main tubular portion 197. As noted above, the guidewire can also extend through the nosecone 110 and the lumen of the inner shaft 108.

The side tubular portion 198 is fluidly coupled to the lumen of the balloon shaft 106. Thus, side tubular portion 198 can serve as a balloon inflation port, through which an inflation fluid can be injected (e.g., via a syringe) into the balloon shaft 106. In some embodiments, the source of the inflation fluid, such as a syringe, can be fluidly coupled to the inflation portion 198 by medical tubing, as known in the art. As described above with reference to FIG. 5, the injected inflation fluid can flow through the annular space 128 between the balloon shaft 106 and the inner shaft 106 and into the balloon 126, thereby inflating the balloon 126. Conversely, the injected inflation fluid can be withdrawn (e.g., via a syringe) from the side tubular portion 198 so as to deflate the balloon 126.

Figure 17:
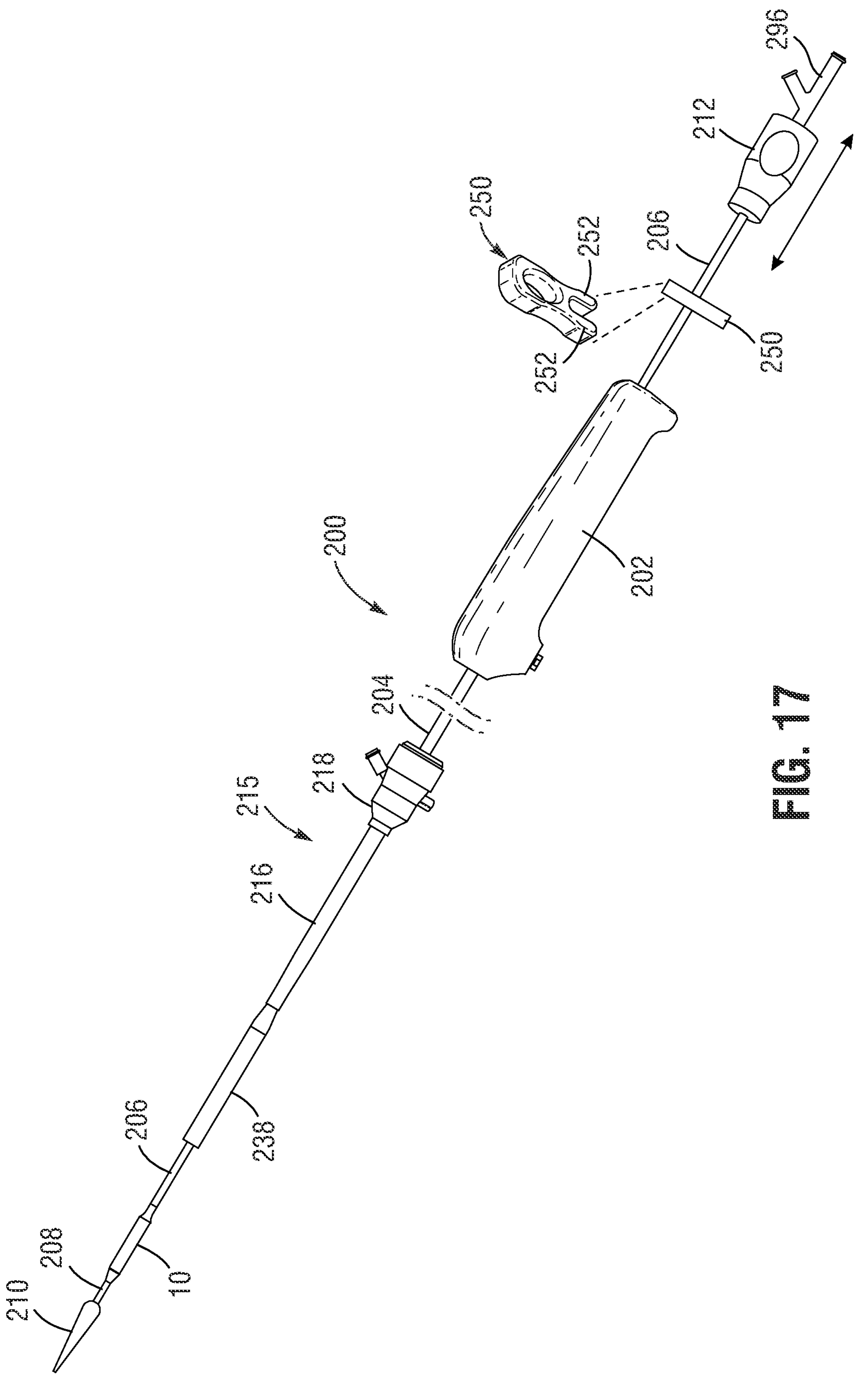
FIG. 17 is a perspective view of a prosthetic valve delivery apparatus, according to another embodiment.

FIG. 17 shows a delivery apparatus 200, according to another embodiment, that can be used to deliver a prosthetic valve, such as the prosthetic valve 10. Similar to the delivery apparatus 100, the delivery apparatus 200 can include a handle 202, an outer shaft 204 connected to the distal end of the handle 202, an intermediate or balloon shaft 206 extending through a lumen of the outer shaft 204, an inner shaft 208 extending through a lumen of the balloon shaft 206, and a nosecone 210 connected to the distal end of the inner shaft 208. Similarly, the delivery apparatus 200 can include a gripper 212 which is located proximal to the handle 202 and is axially moveable relative to the handle 202. Likewise, the delivery apparatus 200 can include a valve sheath or capsule 238 connected to the distal end of the outer shaft 204 and configured to cover the prosthetic valve 10 when the prosthetic valve is compressed over a balloon along the distal end portion of the delivery apparatus 200. In addition, the delivery apparatus 200 can include an inline introducer 215 comprising a sheath 216 and a hub 218. The outer shaft 204 can extend through the inline introducer 215 and can be axially moveable relative to the introducer 215.

In contrast to the delivery apparatus 100 where the Y-connector 196 is disposed within the gripper 112, the delivery apparatus 200 has a Y-connector 296 that is separate from (disposed outside of) the gripper 212. Further, in contrast to the delivery apparatus 100 which has a locking mechanism 150 integrated into the handle 102, the delivery apparatus 200 can have a removable locking member 250 that is a separate component from the handle 202. For example, the locking member 250 can have a pair of resilient prongs 252, which are separated from each other by a distance that is slightly smaller than the diameter of the balloon shaft 206. Thus, by placing the prongs 252 of the locking member 250 against the shaft 206 and pressing the locking member 250 firmly against the shaft 206, the prongs 252 will splay apart and slide along opposite sides of the shaft until the shaft 206 is located between the prongs 252. In this manner, the prongs 252 form a snap-fit connection with the shaft 206. Once placed on the shaft, the prongs 252 frictionally engage the outer surface of the shaft and resist axial movement of the locking member along the length of the shaft. Thus, when the locking member 250 is on the shaft, distal movement of the shaft 206 and the gripper 212 relative to the handle 202 is limited by contact between the locking member 250 and the proximal end of the handle 202. The locking member 250 can be manually removed from the shaft 206 by pulling the locking member away from the shaft in a lateral direction (i.e., perpendicular to the length of the shaft 206).

In some embodiments, the delivery apparatus 200 can include a hypotube (e.g., hypotube 182) that extends over the balloon shaft 206, similar to the hypotube 180 of the delivery apparatus 100, in which case the locking member 250 can be placed on the hypotube to limit distal movement of the hypotube and the balloon shaft 206.

Prior to insertion into a patient, the prosthetic valve 10 can be crimped around the balloon and the delivery sheath 238 can be advanced over the prosthetic valve so that it abuts the nose cone 210 (similar to FIG. 2). The locking member 250 can then be placed on the shaft 206 adjacent the proximal end of the handle 202. In this position, the locking member 250 can prevent distal movement of the shaft 206 and the prosthetic valve 10 relative to the handle 202 and the delivery sheath 238 and/or proximal movement of the handle 202 and the delivery sheath 238 relative to the shaft 206 and the prosthetic valve 10 to prevent premature advancement of the prosthetic valve 10 from the delivery sheath 238. The prosthetic valve 10 and the distal end portion of the delivery apparatus 200 can be then be inserted into the patient's vasculature and advanced to the implantation site. When the prosthetic valve is at or adjacent the implantation site, the locking member 250 can be removed from the shaft 206. Thereafter, the user can advance the prosthetic valve 10 from the delivery sheath 238 by pushing the gripping 212 distally relative to the handle 202 and/or pulling the handle 202 proximally relative to the gripper 212.

In some embodiments, the prosthetic valve 10 can be mounted in a compressed state on the distal end of the delivery device 100 (or 200) and advanced through the patient's vasculature (e.g., through a femoral artery and the aorta) until the prosthetic valve 10 reaches the target implantation site in the heart. The prosthetic valve 10 can then be expanded to its functional size by inflating the balloon on which the prosthetic valve 10 is mounted.

In another embodiment, a docking device or a docking station can be implanted at a target implantation site first. The docking device can then provide a landing zone into which the prosthetic valve 10 can be deployed, as described below. Such approach can be particularly helpful for transcatheter implantation of prosthetic valves at the sites with large annulus, where the prosthetic valve may not be large enough to sufficiently expand inside the native valve or other implantation or deployment site to be secured in place. One such example is replacing the pulmonary valve, which presents significant challenges because the pulmonary artery can have a wide variety of different shapes and sizes. These differences can be even more significant in pulmonary arteries that suffer from certain conditions and/or have been compromised by previous surgery. For example, the treatment of Tetralogy of Fallot (TOF) or Transposition of the Great Arteries (TGA) often results in larger and more irregularly shaped pulmonary arteries.

Figure 18:
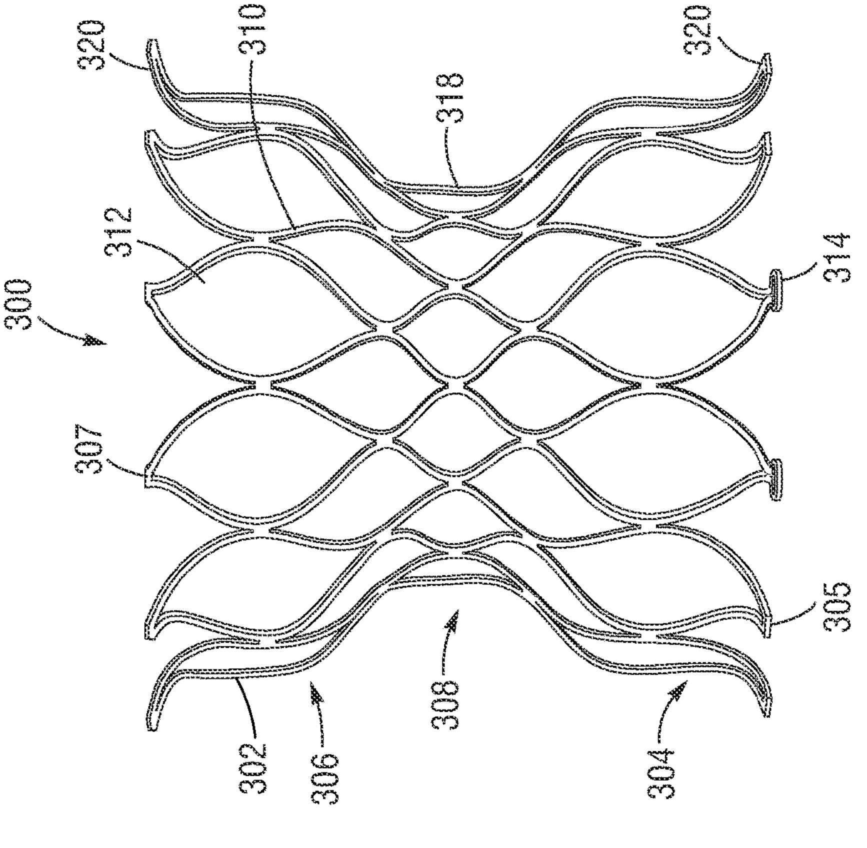
FIG. 18 is a side elevation view of a docking stent, according to one embodiment.

FIG. 18 shows one exemplary embodiment a docking device 300 configured to receive another transcatheter device, such as a transcatheter prosthetic valve 10. The docking device 300 includes an expandable frame 302, which is shown in its unconstrained, expanded condition. When expanded, the frame 302 can be configured or shaped to conform to an interior shape of a portion of the vasculature in which it is to be implanted, such as the pulmonary annulus. The frame 302 is desirable a wide stent comprised of a plurality of metal struts 310 that form cells 312. The docking device 300 can include one or more sealing members 316 (see FIG. 19), which can be made of fabric, polymer, or other covering and are attached to a portion of the frame 302. The sealing members 316 can be configured to contact an interior surface of the circulatory system at the implantation site so as to inhibit or prevent paravalvular leakage.

The expandable frame 302 can be made from a highly resilient or compliant material to accommodate large variations in the anatomy. For example, the frame 302 can be made from a highly flexible metal, metal alloy, polymer, or an open cell foam. An example of a highly resilient metal is nitinol, but other metals and highly resilient or compliant non-metal materials can also be used. In the depicted embodiment, the frame 302 is self-expandable. In other embodiments, the frame can be manually expandable (e.g., expandable via balloon), or mechanically expandable. A self-expanding frame 302 may be made of a shape memory material such as, for example, nitinol.

The docking device 300 can also optionally include one or more valve seats 318 configured to receive and support the transcatheter prosthetic valve 10 after the docking device 300 is implanted in the circulatory system. The valve seats 318 can be attached to the frame 302 or integrally formed with the frame 302. In addition, the docking device 300 can include one or more retaining members 320, which can be any structure that sets the position of the docking device 300 in the circulatory system. In some embodiments, the retaining members 320 can be part of or define a portion of the frame 302 and/or sealing portion of the docking device 300. In some embodiments, the retaining members 320 can be a separate component that is attached to the frame 302 of the docking device 300. In the depicted example, the retaining members 320 comprise free ends of the metal struts 310 at the proximal inflow end 305 and distal outflow end 307 of the frame 302. For example, the retaining members 302 can press against or into the inside surface or contour/extend around anatomical structures of the circulatory system to set and maintain the position of the docking device 300.

In the depicted example, when fully expanded, the frame 302 can have an hourglass shape defined by a relatively wider proximal inflow portion 304 and distal outflow portion 306, and a relatively narrower waist portion 308 between the inflow and outflow portions 302 and 304. In certain embodiments, the narrow waist portion 308 can form the valve seat 318 when covered by an impermeable material, and the prosthetic valve 10 can expand in the narrow waist portion 308. The frame 302 can also include one or more retaining tabs 314 extending from the inflow end 305 (or alternatively from the outflow end 307), which can be releasably connected to a retaining member of a delivery catheter, as described below.

The illustrated docking device 300 and prosthetic valve 10 are particularly suited to be deployed in the pulmonary artery or right ventricular outflow tract for pulmonary valve replacement. However, the docking device 300 and prosthetic valve 10 can be deployed in any interior surface within the heart or a lumen of the body. For example, the various docking devices and valves described herein can be deployed in the superior vena cava, the inferior vena cava, the tricuspid valve, the mitral valve, the aortic valve, aorta, or other vasculature/lumens in the body. Further details regarding the docking device are disclosed in U.S. Patent Publications Nos. 2017/0231756 and 2019/0000615, which are incorporated herein by reference.

Figure 19:
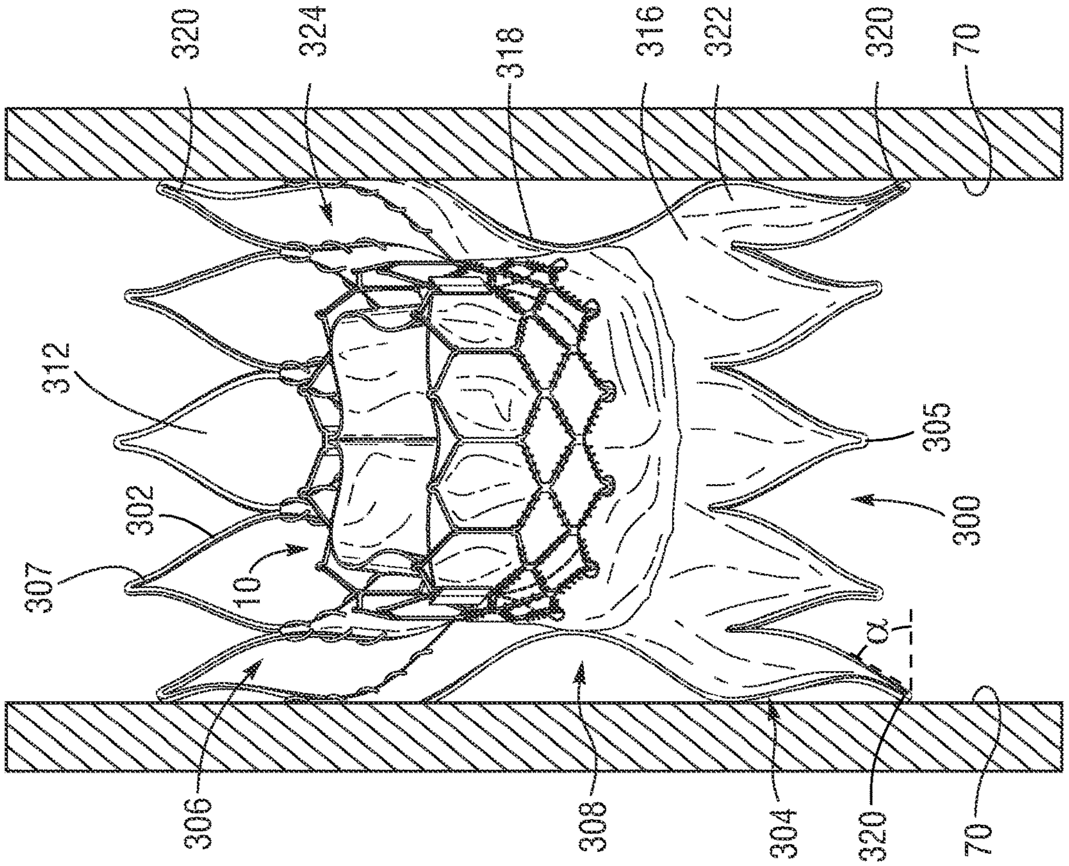
FIG. 19 is a side view of a prosthetic valve retained by the docking stent of FIG. 20, which is shown anchored at an annulus of a native valve, according to one embodiment.

As an example, FIG. 19 illustrates the prosthetic valve 10 received within the docking device 300 implanted in the circulatory system, such as in the pulmonary artery. In the depicted embodiment, a sealing member 316 provides a seal between the docking device 300 and an interior surface 70 of the circulatory system. The sealing members 316 can be formed by providing a blood impermeable material (e.g., a PET cloth) over the frame 302 or a portion thereof. In particular embodiments, the sealing member 316 can cover the lower (near the inflow end 305), rounded, radially outward extending portion 322 of the frame 302. In an exemplary embodiment, the sealing member 316 can extend from at least the portion 322 of the frame 302 to the valve seat 318. This makes the docking device 300 impermeable from the portion 322 to the valve seat 318. As such, all blood flowing in the direction from the inflow end 305 toward the outflow end 307 is directed to the valve seat 318 (and the prosthetic valve 10 once installed or deployed in the valve seat 318).

In certain embodiments, the walls at the inflow portion 304 of the docking device 300 are impermeable to blood, but the walls at the outflow portion 306 are relatively open. In one embodiment, the inflow portion 304, the waist portion 308, and a portion of the outflow portion 306 are covered with a blood-impermeable fabric, which may be sewn onto the frame 302 or otherwise attached by a method known in the art. The impermeability of the inflow portion 304 of the frame 302 can help funnel blood into the docking device 300 and ultimately flow through the valve 10 that is to be expanded and secured within the docking device 300.

From another perspective, this embodiment of a docking device is designed to seal at the proximal inflow portion 304 to create a conduit for blood flow. However, at least some of the distal rows of cells 312 can be generally left open and form a permeable portion 324, thereby allowing the docking device 300 to be placed higher in the pulmonary artery without restricting blood flow. For example, the distal permeable portion may extend into the branch of the pulmonary artery and not impede or not significantly impede the flow of blood past the branch. In one embodiment, blood-impermeable cloth, such as a PET cloth for example, or other material covers the proximal inflow portion 304, but the covering does not cover any or at least a portion of the distal outflow portion 306. As one non-limiting example, when the docking device 300 is placed in the pulmonary artery, which is a large vessel, the significant volume of blood flowing through the artery is funneled into the valve 10 by the sealing member 316. The sealing member 316 is fluid impermeable so that blood cannot pass through. Again, a variety of other biocompatible covering materials may be used such as, for example, foam or a fabric that is treated with a coating that is impermeable to blood, polyester, or a processed biological material, such as pericardium.

The valve seat 318 can provide a supporting surface for implanting or deploying the prosthetic valve 10 in the docking device 300. The retaining members 320 can retain the docking device 300 at the implantation position or deployment site in the circulatory system. For example, the illustrated retaining members 320 have an outwardly curving flare that helps secure the docking device 10 within the pulmonary artery. In the depicted embodiment, when the docking device 300 is compressed by the interior surface 70, the retaining members 320 can engage the surface 70 at an angle $\alpha$ (between the normal direction to the surface 70 and the tangent of the retaining member 320) that can range between about 30 and 60 degrees, such as about 45 degrees. This inward bending of the retaining members 320 acts to retain the docking device 300 in the circulatory system. The retaining members 320 are at the wider inflow end 305 and outflow end 307 and press against the interior surface 70. The flared retaining members 320 can engage into the surrounding anatomy in the circulatory system, such as the pulmonary space. In one exemplary embodiment, the flares can serve as a stop, which locks the device 300 in place. When an axial force is applied to the docking device 300, the flared retaining members 320 are pushed by the force into the surrounding tissue to resist migration of the docking device 300.

Figure 20:
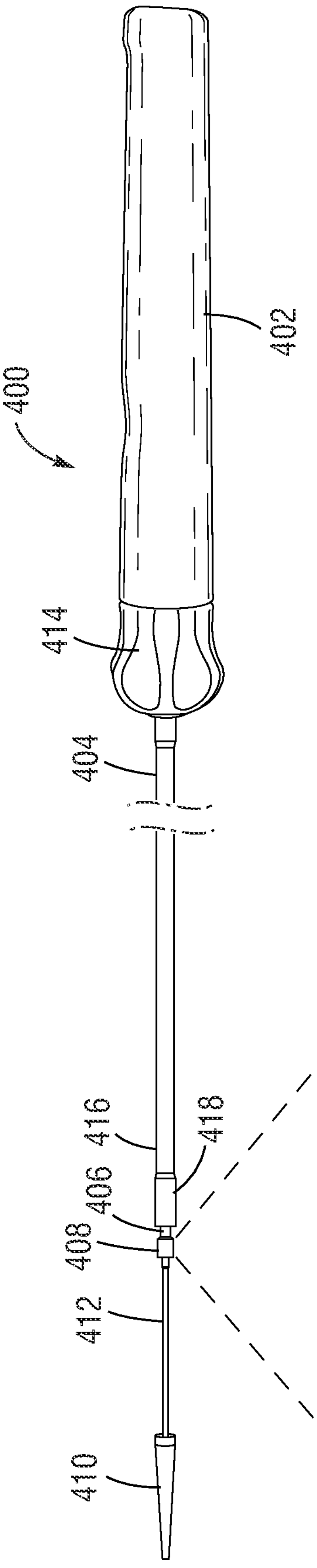
FIG. 20 is a side elevation view of a delivery apparatus for a docking stent, according to one embodiment.

FIG. 20 shows an exemplary embodiment of a delivery apparatus 400 for delivering and deploying the docking device 300. The delivery apparatus 400 can take a wide variety of different forms. In the illustrated example, the delivery apparatus 400 includes a handle 402, an outer shaft 404 connected to the handle 402, an inner shaft 406 extending through a lumen of the outer shaft 404, a docking device retaining member 408 that is connected to the inner shaft 406, and a nosecone 410 that is connected to the docking device retaining member 408 by a connecting tube 412. The outer shaft 404 can be axially moveable relative to the inner shaft 406, for example, by rotating a drive member 414 (e.g., a rotatable knob) located on the handle 402. The distal end portion 416 of the outer shaft 404 can form a delivery sheath or capsule that is configured to extend over the docking device 300 during delivery. In addition, a guidewire 420 (see FIG. 21A) can extend through a lumen of the inner shaft 406 and the nosecone 410 such that the inner shaft 406 and outer shaft 404 can be routed over the guidewire to position the docking device 300 at the implantation site.

Figure 20A:
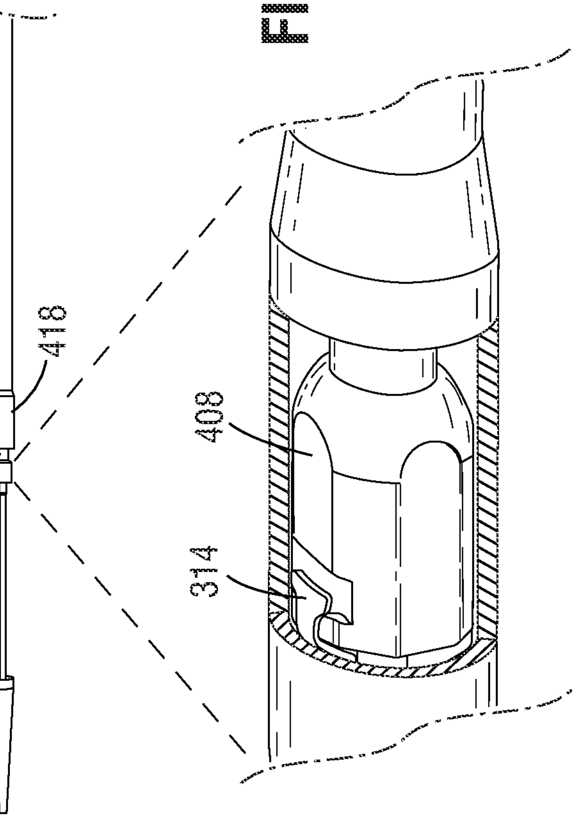
FIG. 20A is an enlarged view of a valve connecting portion of the delivery apparatus depicted in FIG. 20.

In a delivery configuration, the docking device 300 can be disposed along a distal end portion of the inner shaft 406 and retained in a compressed configuration by the delivery sheath 416, which extends cover the radially compressed docking device. The retaining tabs 314 of the frame 302 can be releasably connected to the docking device retaining member 408 (see FIG. 20A). A radiopaque marker 418 can be placed along the delivery sheath 416, either on the outer surface of the delivery sheath or embedded within the wall of the delivery sheath. The outer shaft 404 can be progressively retracted (e.g., by actuating the drive member 414) in a proximal direction relative to the inner shaft 406, the retaining member 408, and the nosecone 410 to deploy the docking device 300, as described below. Further details regarding the delivery apparatus 400 and methods for implanting the docking device 300 are disclosed in U.S. Patent Publications Nos. 2017/0231756 and 2019/0000615.

FIGS. 21A-21H illustrate certain steps of implanting the docking device 300 and the prosthetic valve 10 at the RVOT for pulmonary valve replacement, according to one embodiment.

Figure 21A:
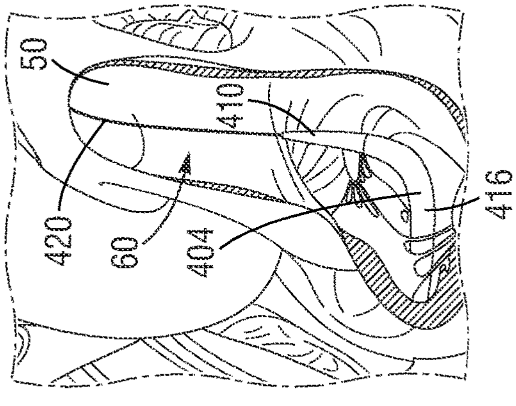
FIG. 21A shows introducing a first delivery apparatus into a pulmonary artery, according to one embodiment.

FIG. 21A shows a guidewire 420 inserted through a patient's vasculature and into the pulmonary bed. Specifically, the guidewire 420 can be advanced to the pulmonary artery 50 by way of the femoral vein, inferior vena cava, right atrium, tricuspid valve, right ventricle, and the right ventricular outflow tract. Under fluoroscopy, the delivery apparatus 400 (only the outer shaft 404 and the nosecone 410 are shown) that retains the docking device 300 can be delivered over the guidewire 420. The delivery apparatus 400 can be advanced until the radiopaque marker 418 is positioned at a distal end of the intended landing zone 60 where the docking device 300 is to be deployed.

Figure 21B:
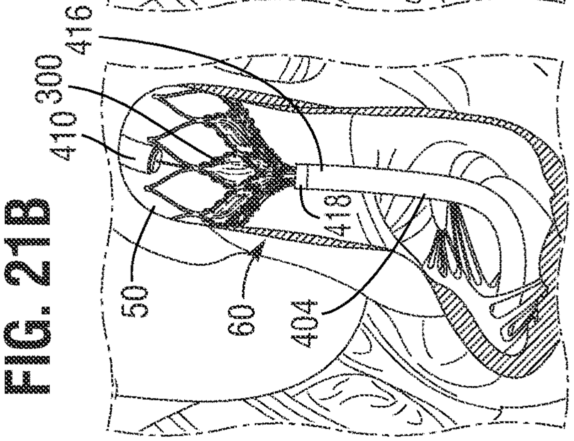
FIG. 21B shows partially expanding a docking stent from the first delivery apparatus at a location corresponding to the native pulmonary valve, according to one embodiment.

Then, as shown in FIG. 21B, the outer shaft 404 can be progressively retracted (e.g., by rotating the drive member 414 in a first direction) with respect to inner shaft 406 to deploy the docking device 300. As the distal portion of the docking device 300 becomes uncovered by the outer shaft 404, the distal portion of the frame 302 begins to self-expand. When the radiopaque marker 416 is at about the waist portion 308 of the frame 302, the distal half the frame 302 is fully expanded at the intended landing zone 60. When the frame is partially expanded, the deployment position of the docking device 300 can be reassessed. If repositioning of the docking device 300 is needed, the distal portion of the frame 302 can be compressed and recaptured by the delivery sheath 416 of the outer shaft 404. This can be achieved, for example, by moving the outer shaft 404 distally (e.g., by rotating the drive member 414 in a second direction opposite the first direction) until it contacts the nosecone 410. Then the radiopaque marker 418 can be repositioned relative to the intended landing zone 60 to redeploy the docking device 300.

Figure 21C:
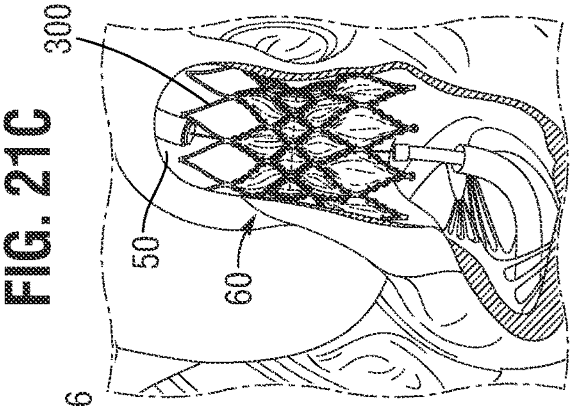
FIG. 21C shows fully expanding the docking stent at the location corresponding to the native pulmonary valve, according to on embodiment.

Further retracting the outer shaft 404 past the waist portion 308 can release the proximal half of the frame 302 from the delivery sheath 416. When the outer shaft 404 is retracted to a position that exposes the retaining tabs 314, the retaining tabs 314 can be released from the docking device retaining member 408 due to the expanding force of the frame 302. Thus, as shown in FIG. 21C, the frame 302 can be fully expanded and frictionally engage the inner wall of the pulmonary artery (or right ventricular outflow tract), i.e., the docking device 300 is fully deployed at the intended landing zone 60.

Figure 21D:
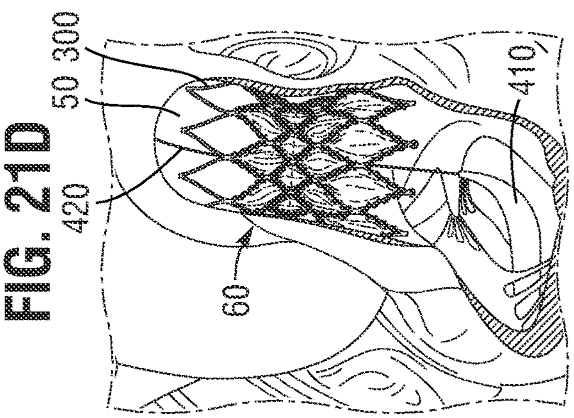
FIG. 21D shows withdrawing the first delivery apparatus from the pulmonary artery, according to one embodiment.

As shown in FIG. 21D, after deploying the docking device 300 at the intended landing zone 60, the delivery apparatus 400 can be retracted from the patient's vasculature over the guidewire 420 while leaving the guidewire 420 in place. After withdrawing the delivery apparatus 400 from the patient's vasculature, the prosthetic valve 10 can then be delivered to and received by the docking device 300 via the delivery apparatus 100, as described below (although the delivery apparatus 100 is described as an example for illustration, similar steps can be performed using the delivery apparatus 200).

Before implanting the prosthetic valve 10, the prosthetic valve 10 can be crimped on the balloon 126 and covered by the valve sheath 138 of the delivery apparatus 100 (see e.g., FIG. 1). For pulmonary valve implantation, the prosthetic valve 10 is oriented so that its inflow end 22 is located proximal to the outflow end 24 when the valve 10 is crimped on the valve retaining portion 130 of the balloon 126 (see e.g., FIG. 4B). The gripper 112 and the handle 102 are axially separated from each other until the distal end 138*d* of the valve sheath 138 contacts the engagement end 111 of the nosecone 110 so that the valve sheath 138 completely covers the prosthetic valve 10. Then, the locker body 152 on the handle 102 can be turned to the locked position so that the handle 102 and the gripper 112 are not axially moveable relative to each other. Thus, the nosecone 110 and the valve sheath 138 are locked together when navigating through patient's vasculature.

In one example embodiment, the nosecone 110, the valve sheath 138, and the sheath 116 of the inline introducer 115 are inserted together into the patient's vasculature (e.g., through a surgical opening in a femoral vein) as a single unit over the guidewire 420, desirably with the distal end 116*d* of the sheath 116 adjacent or abutting the proximal end 138*p* of the valve sheath 138.

After the sheath 116 is fully inserted into the vasculature (with the hub 118 remaining outside the patient's body), the hub 118 can be secured in place relative to the patient and/or the operating table (e.g., by clamping or other means).

Figure 21E:
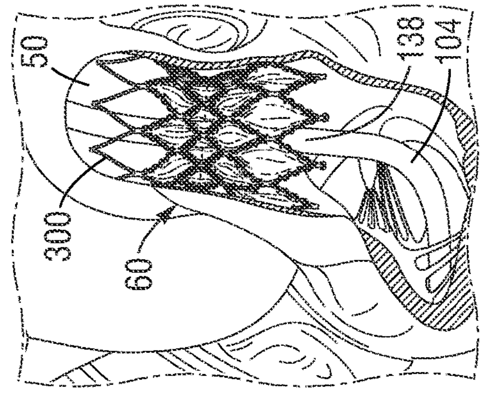
FIG. 21E shows introducing a second delivery apparatus carrying a prosthetic valve into the pulmonary artery, according to one embodiment.

Thereafter, the shafts 104, 106, 108 of the delivery apparatus 100 can be advanced over the guidewire 420 and relative to the sheath 116 through the patient's vasculature (e.g., by pushing the outer shaft 104 or the handle 102) until the valve sheath 138 is positioned at the intended landing zone 60 marked by the pre-implanted docking device 300, as shown in FIG. 21E. Because the handle 102 is locked and cannot move relative to the gripper 112, the outer shaft 104 (which is connected to the handle) and the valve sheath 138 (which is connected to the outer shaft 104) cannot move axially relative to the balloon shaft 106 and the inner shaft 108 (both of which are connected to the gripper). Thus, during the advancement, the prosthetic valve 10 remains covered by the valve sheath 138 so as to protect against damage to the prosthetic valve as well as the inner wall of the vasculature and the tricuspid valve chordae tendineae.

After reaching the intended landing zone 60, the delivery apparatus 100 can be manipulated so that the prosthetic valve 10 is placed within the waist 308 region of the docking device 300. This can be confirmed, for example, by aligning the radiopaque marker 136 of the delivery apparatus 100 with the middle (i.e., the narrowest part) of the waist region 308 based on the fluoroscopic views.

Figure 21F:
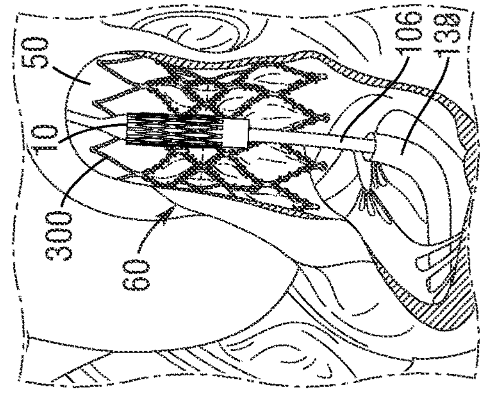
FIG. 21F shows retracting a sheath of the second delivery apparatus to expose the prosthetic valve and positioning the prosthetic valve within the docking stent, according to one embodiment.

Then, as shown in FIG. 21F, the outer shaft 104 and the valve sheath 138 connected thereto can be retracted in the proximal direction to uncover the prosthetic valve 10. To retract the outer shaft 104 and the valve sheath 138, the locker body 152 on the handle 102 can be turned to the unlocked position so that the handle 102 and the gripper 112 are axially moveable relative to each other. Therefore, by holding the gripper 112 stationary (thus maintaining the position of the balloon shaft 106) while moving the handle 102 in the proximal direction, the outer shaft 104 and the valve sheath 138 can be retracted proximally relative to the balloon shaft 106 and the prosthetic valve 10. Retraction of the outer shaft 104 and valve sheath 138 can be continued until the proximal end 114 of the handle 102 abuts the distal end 112*d* of the gripper 112, whereby the valve sheath 138 is moved to the uncovered position and the prosthetic valve 10 is fully uncovered. Alternatively, the prosthetic valve 10 can be deployed from the valve sheath 138 by pushing the gripper 112 distally relative to the handle 102.

Figure 21G:
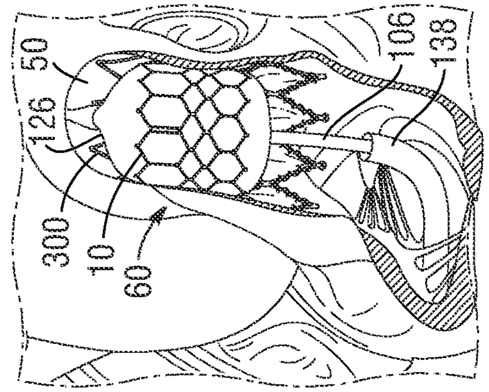
FIG. 21G shows expanding the prosthetic valve within the docking stent member using an inflatable balloon of the second delivery apparatus, according to one embodiment.

As shown in FIG. 21G, after the prosthetic valve 10 is uncovered by the valve sheath 138, the balloon 126 can be inflated, e.g., by injecting an inflation fluid into the balloon shaft 106 (e.g., through the balloon inflation port 198, as shown in FIG. 14). Inflation of the balloon 126 can cause radial expansion of the prosthetic valve 10 within the interior of the docking device 300. In some embodiments, a slow controlled inflation of the balloon 126 may be administered during initial deployment of the prosthetic valve 10 to improve the stability of the delivery system and the prosthetic valve 10. The fully expanded prosthetic valve 10 can be received by the docking device 300. The position of the prosthetic valve 10 can be verified under fluoroscopy. If repositioning is necessary, the handle 102 and the gripper 112, which can be held together as a single unit (i.e., they remain contact with each other), can be manipulated to slightly adjust the position and/or angle of the balloon shaft 106 and the prosthetic valve 10 as needed to ensure a secure fitting between the prosthetic valve 10 and the docking device 300.

Figure 21H:
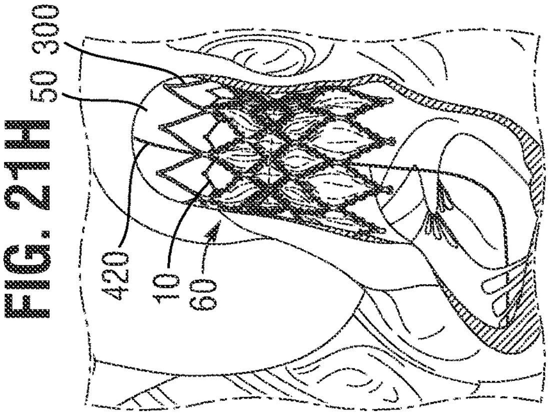
FIG. 21H shows withdrawing the second delivery apparatus from the pulmonary artery, according to one embodiment.

As shown in FIG. 21H, after the prosthetic valve 10 is fully expanded and securely docked to the docking device 100, the balloon 126 can be deflated, e.g., by withdrawing the inflation fluid out of the balloon 126 and the balloon shaft 106. The shafts 104, 106, 108 of the delivery apparatus 100 can be retracted, over the guidewire 420, into the vena cava while maintaining the contact between the handle 102 and the gripper 112. Then the deflated balloon 126 can be resheathed (i.e., captured or covered) by the valve sheath 138.

Resheathing of the balloon 126 can be achieved, for example, by moving the gripper 112 in the proximal direction while holding the handle 102 stationary until the engagement end 111 of the nosecone 110 abuts the distal end 138*d* of the valve sheath 138. As noted above, the distance between the flared portion 184 and the gripper 112 desirably is equal to or greater than the axial distance (D1) between the distal end 138*d* of the valve sheath 138 and the engagement end 111 of the nosecone 110 when the valve sheath 138 is in the uncovered position (see e.g., FIG. 3). Thus, when proximal movement of the gripper 112 relative to the handle 102 is restricted because the flared portion 184 engages the end plate 172 inside the handle 102 (see e.g., FIG. 15B), it indicates that the engagement end 111 of the nosecone 110 contacts the distal end 138*d* of the valve sheath 138, i.e., the balloon 126 is fully covered by the valve sheath 138. In addition to or in lieu of relying the engagement between the flared portion 184 and the end plate 172, the observation of the marker band 183 in the gap between the gripper 112 and the handle 102 can also indicate the end of hypotube travel and provide a visual confirmation that balloon is fully resheathed. Resheathing the balloon 126 can facilitate smooth retraction of the delivery apparatus 100 and prevent damage to the inner wall of the vasculature and the tricuspid valve chordae tendinae during the retraction.

After resheathing the balloon 126, the shafts 104, 106, 108 of the delivery apparatus 100 can be retracted further as a single unit until the proximal end 138*p* of the valve sheath 138 abuts the distal end 116 of the sheath 116 (see e.g., FIG. 8). Then, the entire delivery apparatus 100, including the shafts 104, 106, 108 and the sheath 116, can be retracted together out of the patient's vasculature. The guidewire 420 can then be removed as well.

General Considerations

It should be understood that the disclosed embodiments can be adapted to deliver and implant prosthetic devices in any of the native annuluses of the heart (e.g., the pulmonary, mitral, and tricuspid annuluses), and can be used with any of various delivery approaches (e.g., retrograde, antegrade, transseptal, transventricular, transatrial, etc.).

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. The technologies from any example can be combined with the technologies described in any one or more of the other examples. In view of the many possible embodiments to which the principles of the disclosed technology may be applied, it should be recognized that the illustrated embodiments are only preferred examples and should not be taken as limiting the scope of the disclosed technology.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "connected" generally mean electrically, electromagnetically, and/or physically (e.g., mechanically or chemically) coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or", as well as "and" and "or".

As used herein, two lengths are deemed substantially identical if the difference between the two lengths is smaller than 10% of the average of the two lengths.

Additional Examples of the Disclosed Technology

In view of the above-described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A delivery apparatus for implanting a prosthetic valve comprising: a handle; a first shaft extending from a distal end of the handle; a second shaft extending through a lumen of the first shaft and the handle; and a gripper located proximal to a proximal end of the handle; wherein a proximal end of the second shaft is connected to the gripper, and the gripper is axially moveable relative to the handle such that axial movement of the gripper causes corresponding axial movement of the second shaft relative to the first shaft; wherein the gripper has a bottom surface that is substantially coplanar with a bottom surface of the handle.

Example 2. The delivery apparatus of any example herein, particularly example 1, wherein a distance from a longitudinal axis of second shaft to the bottom surface of the gripper is substantially identical to a distance from a longitudinal axis of the first shaft to the bottom surface of the handle.

Example 3. The delivery apparatus of any example herein, particularly any one of examples 1-2, wherein the first shaft comprises a proximal section, a distal section, and an intermediate section between the proximal and distal sections, wherein the distal section is more flexible than the intermediate section and the intermediate section is more flexible than the proximal section.

Example 4. The delivery apparatus of any example herein, particularly any one of examples 1-3, further comprising an inflatable balloon, the balloon having a valve retaining portion configured to mount the prosthetic valve thereto.

Example 5. The delivery apparatus of any example herein, particularly example 4, further comprising a valve sheath configured to cover the prosthetic valve when the prosthetic valve is mounted on the balloon in a radially compressed state, wherein a proximal end of the valve sheath is connected to a distal end of the first shaft.

Example 6. The delivery apparatus of any example herein, particularly example 5, wherein when the prosthetic valve is covered by the valve sheath, a distance between the proximal end of the handle and the gripper is equal to or greater than a length of the valve sheath such that when the proximal end of the handle contacts the gripper after axially moving the handle relative to the gripper, a distal end of the valve sheath is located proximal to a proximal end of the prosthetic valve, thereby completely uncovering the prosthetic valve.

Example 7. The delivery apparatus of any example herein, particularly any one of examples 5-6, further comprising a third shaft extending through a lumen of the second shaft, wherein a proximal end of the third shaft is connected to the gripper and a distal end of the third shaft is connected to a nosecone.

Example 8. The delivery apparatus of any example herein, particularly example 7, further comprising a balloon shoulder assembly, wherein the balloon shoulder assembly comprises a proximal shoulder connected to a distal end portion of the second shaft and a distal shoulder connected to a distal end portion of the third shaft, wherein the distal and proximal shoulders are disposed inside the balloon.

Example 9. The delivery apparatus of any example herein, particularly example 8, wherein the third shaft comprises a radiopaque marker located between the proximal shoulder and the distal shoulder.

Example 10. The delivery apparatus of any example herein, particularly any one of examples 7-9, wherein a proximal end of the nosecone abuts a distal end of the valve sheath when the prosthetic valve is retained inside the valve sheath.

Example 11. The delivery apparatus of any example herein, particularly any one of examples 1-10, wherein the gripper comprises a housing defining the bottom surface of the gripper, the gripper further comprising a Y-connector having a main tubular portion and a side tubular portion, the side tubular portion being fluidly connected to and extending angularly from the main tubular portion, wherein the main tubular portion extends through the gripper housing and is substantially parallel to the bottom surface of the gripper housing, and the side tubular portion extends through an opening on top surface of the gripper housing.

Example 12. The delivery apparatus of any example herein, particularly example 11, wherein the proximal end of the second shaft is connected to the main tubular portion of the Y-connector.

Example 13. The delivery apparatus of any example herein, particularly any one of examples 1-12, further comprising an introducer mounted on the first shaft, the introducer comprising a sheath and a hub connected to a proximal end of the sheath, wherein the first shaft extends through and is axially movable relative to the sheath and the hub.

Example 14. The delivery apparatus of any example herein, particularly any one of examples 1-13, wherein the handle comprises a locking mechanism, the locking mechanism comprising a locker body that is moveable between a locked position and an unlocked position, wherein when the locker body is in the unlocked position, the second and fourth shafts are axially moveable relative to the handle and the first shaft, and wherein when the locker body is in the unlocked position, the second and fourth shafts are not axially movable relative to the first shaft and the handle.

Example 15. The delivery apparatus of any example herein, particularly example 14, further comprising a fourth shaft extending through the handle, wherein a proximal end of the fourth shaft is connected to the gripper and the second shaft extends through the fourth shaft.

Example 16. The delivery apparatus of any example herein, particularly example 15, wherein the locker body comprises a user-engageable tab, wherein the locking mechanism further comprises at least one detent element positioned to engage the tab when the locker body is in the locked position or the unlocked position.

Example 17. The delivery apparatus of any example herein, particularly example 16, wherein the at least one detent element comprises a first detent element adjacent the locked position and a second detent element adjacent the unlocked position, wherein rotating the tab across the first detent element in a first angular direction causes the tab to align with the locked position and rotating the tab across the second detent element in a second angular direction causes the tab to align with the unlocked position, the second angular direction being opposite the first angular direction.

Example 18. The delivery apparatus of any example herein, particularly any one of examples 15-17, wherein the locking mechanism further comprises a collet that is at least partially received within the locker body, wherein the collet comprises external threads engaging internal threads of the locker body and is coaxially disposed around the fourth shaft, wherein rotation of the locker body produces axial movement of the collet relative to the locker body and the fourth shaft.

Example 19. The delivery apparatus of any example herein, particularly example 18, wherein the collet has a distal opening through which the fourth shaft extends, the fourth shaft comprises a flared portion, wherein the flared portion has a diameter that is larger than a diameter of the distal opening such that proximal movement of the fourth shaft is blocked when the flared portion abuts the collet.

Example 20. The delivery apparatus of any example herein, particularly any one of examples 15-19, wherein an interior surface of the locker body defines a locker lumen, the locker lumen having a proximal portion and a distal portion, wherein the locker lumen has a tapered shape such that the proximal portion has a smaller diameter than the distal portion.

Example 21. A delivery apparatus for implanting a prosthetic valve comprising: a handle; a first shaft extending from a distal end of the handle; a second shaft extending through a lumen of the first shaft and the handle; and a gripper located proximal to a proximal end of the handle; wherein a proximal end of the second shaft is connected to the gripper, and the gripper is axially moveable relative to the handle such that axial movement of the gripper causes corresponding axial movement of the second shaft relative to the first shaft; wherein a distance from a longitudinal axis of second shaft to a bottom surface of the gripper is substantially identical to a distance from a longitudinal axis of the first shaft to a bottom surface of the handle.

Example 22. The delivery apparatus of any example herein, particularly example 21, further comprising an inflatable balloon, the balloon having a valve retaining portion configured to mount the prosthetic valve thereto.

Example 23. The delivery apparatus of any example herein, particularly example 22, further comprising a valve sheath configured to cover the prosthetic valve when the prosthetic valve is mounted on the balloon in a radially compressed state, wherein a proximal end of the valve sheath is connected to a distal end of the first shaft.

Example 24. The delivery apparatus of any example herein, particularly example 23, wherein when the prosthetic valve is covered by the valve sheath, a distance between the proximal end of the handle and the gripper is equal to or greater than a length of the valve sheath such that when the proximal end of the handle contacts the gripper after axially moving the handle relative to the gripper, a distal end of the valve sheath is located proximal to a proximal end of the prosthetic valve, thereby completely uncovering the prosthetic valve.

Example 25. The delivery apparatus of any example herein, particularly any one of examples 22-24, further comprising a third shaft extending through a lumen of the second shaft, wherein a proximal end of the third shaft is connected to the gripper and a distal end of the third shaft is connected to a nosecone.

Example 26. The delivery apparatus of any example herein, particularly example 25, further comprising a balloon shoulder assembly, wherein the balloon shoulder assembly comprises a proximal shoulder connected to a distal end portion of the second shaft and a distal shoulder connected to a distal end portion of the third shaft, wherein the distal and proximal shoulders are disposed inside the balloon.

Example 27. The delivery apparatus of any example herein, particularly any one of examples 25-26, wherein a proximal end of the nosecone abuts a distal end of the valve sheath when the valve sheath is in a closed position.

Example 28. The delivery apparatus of any example herein, particularly any one of examples 21-27, wherein the gripper comprises a housing defining the bottom surface of the gripper, the gripper further comprising a Y-connector having a main tubular portion and a side tubular portion, the side tubular portion being fluidly connected to and extending angularly from the main tubular portion, wherein the main tubular portion extends through the gripper housing and is substantially parallel to the bottom surface of the gripper housing, and the side tubular portion extends through an opening on top surface of the gripper housing, wherein the proximal end of the second shaft is connected to the main tubular portion of the Y-connector.

Example 29. The delivery apparatus of any example herein, particularly any one of examples 21-28, wherein the handle comprises a locking mechanism, the locking mechanism comprising a locker body that is moveable between a locked position and an unlocked position, wherein when the locker body is in the unlocked position, the second shaft is axially moveable relative to the handle and the first shaft, and wherein when the locker body is in the unlocked position, the second shaft is not axially movable relative to the first shaft and the handle.

Example 30. The delivery apparatus of any example herein, particularly example 29, wherein the locker body comprises a user-engageable tab, wherein the locking mechanism further comprises at least one detent element positioned to engage the tab when the locker body is in the locked position or the unlocked position.

Example 31. A delivery apparatus for implanting a prosthetic valve comprising: a handle comprising a locking mechanism; a first shaft extending from a distal end of the handle; and a second shaft extending through the handle; wherein the locking mechanism comprises a rotatable locker body having internal threads and a collet at least partially received within the locker body, wherein the collet comprises external threads engaging the internal threads of the locker body and is coaxially disposed around the second shaft, wherein rotation of the locker body produces axial movement of the collet relative to the locker body and the second shaft; wherein the locker body is rotatable between a locked position and an unlocked position, wherein when the locker body is in the unlocked position, the second shaft is axially moveable relative to the handle, the first shaft, and the collet, and wherein when the locker body is in the unlocked position, the collet prevents axial movement of the second shaft relative to the first shaft and the handle.

Example 32. The delivery apparatus of any example herein, particularly example 31, wherein the locker body comprises a cylindrical portion and a tab extending radially outwardly from the cylindrical portion, wherein the second shaft extends through the cylindrical portion, wherein the locking mechanism further comprises at least one detent element positioned to engage the tab when the locker body is in the locked position or the unlocked position.

Example 33. The delivery apparatus of any example herein, particularly example 32, wherein the at least one detent element comprises a first detent element adjacent the locked position and a second detent element adjacent the unlocked position, wherein rotating the tab across the first detent element in a first angular direction causes the tab to align with the locked position and rotating the tab across the second detent element in a second angular direction causes the tab to align with the unlocked position, the second angular direction being opposite the first angular direction.

Example 34. The delivery apparatus of any example herein, particularly any one of examples 32-33, further comprising at least one biasing member configured to bias the at least one detent element in a direction toward the tab.

Example 35. The delivery apparatus of any example herein, particularly any one of examples 32-34, wherein an interior surface of the cylindrical portion defines a locker lumen, the locker lumen having a proximal portion and a distal portion, wherein the locker lumen has a tapered shape such that the proximal portion has a smaller diameter than the distal portion.

Example 36. The delivery apparatus of any example herein, particularly example 35, wherein the collet comprises an end plate, a neck portion extending proximally from the end plate, and a plurality of arms extending proximally from the neck portion, wherein the second shaft extends through an opening on the end plate and a lumen of the neck portion, and the plurality of arms are disposed around the second shaft.

Example 37. The delivery apparatus of any example herein, particularly example 36, wherein the arms and the neck portion are configured to be inserted into the locker lumen, wherein the neck portion is configured to threadably engage the internal threads of the locker body such that rotating the locker body toward the locked position causes the collet to move in a proximal direction and rotating the locker body toward the unlocked position causes the collet to move in a distal direction.

Example 38. The delivery apparatus of any example herein, particularly any one of examples 36-37, wherein the locking mechanism is so configured that when the locker body is in the locked position, distal end portions of the arms are inserted into and compressed radially inwardly by the proximal portion of the locker lumen, and when the locker body is in the unlocked position, the distal end portions of the arms move into the distal portion of the locker lumen and expand radially outwardly.

Example 39. The delivery apparatus of any example herein, particularly any one of examples 36-38, wherein the second shaft comprises a flared portion, the flared portion having a diameter that is larger than a diameter of the opening on the end plate of the collet such that proximal movement of the second shaft is blocked when the flared portion abuts the end plate of the collet.

Example 40. The delivery apparatus of any example herein, particularly any one of examples 31-39, further comprising a gripper located proximal to a proximal end of the handle, wherein a proximal end of the second shaft is connected to the gripper such that axial movement of the gripper causes corresponding axial movement of the second shaft relative to the first shaft when the locker body is in the locked position.

Example 41. A delivery apparatus for implanting a prosthetic valve comprising: a handle comprising a locking mechanism, the locking mechanism comprising a locker body having a user-engageable portion; a first shaft extending from a distal end of the handle; a second shaft extending through the handle; wherein the locker body is moveable between a locked position and an unlocked position, wherein when the locker body is in the unlocked position, the second shaft is axially moveable relative to the handle and the first shaft, and wherein when the locker body is in the unlocked position, the second shaft is not axially movable relative to the first shaft and the handle; and at least one detent element positioned to engage the user-engageable portion when the locker body is in the locked position or the unlocked position.

Example 42. The delivery apparatus of any example herein, particularly example 41, wherein the at least one detent element comprises a first detent element adjacent the locked position and a second detent element adjacent the unlocked position, wherein rotating the tab across the first detent element in a first angular direction causes the tab to align with the locked position and rotating the tab across the second detent element in a second angular direction causes the tab to align with the unlocked position, the second angular direction being opposite the first angular direction.

Example 43. The delivery apparatus of any example herein, particularly example 41, further comprising at least one biasing member configured to bias the at least one detent element in a direction toward the user-engageable portion.

Example 44. The delivery apparatus of any example herein, particularly example 42, further comprising first and second biasing members configured to bias the first and second detent elements in a direction toward the user-engageable portion.

Example 45. The delivery apparatus of any example herein, particularly any one of examples 41-44, wherein the locking mechanism further comprises a collet at least partially received within the locker body, wherein the collet comprises external threads engaging internal threads of the locker body and is coaxially disposed around the second shaft, wherein rotation of the locker body produces axial movement of the collet relative to the locker body and the second shaft.

Example 46. The delivery apparatus of any example herein, particularly example 45, wherein an interior surface of the locker body defines a locker lumen, the locker lumen having a proximal portion and a distal portion, wherein the locker lumen has a tapered shape such that the proximal portion has a smaller diameter than the distal portion.

Example 47. The delivery apparatus of any example herein, particularly example 46, wherein the collet comprises an end plate, a neck portion extending proximally from the end plate, and a plurality of arms extending proximally from the neck portion, wherein the second shaft extends through an opening on the end plate and a lumen of the neck portion, and the plurality of arms are disposed around the second shaft.

Example 48. The delivery apparatus of any example herein, particularly example 47, wherein the arms and the neck portion are configured to be inserted into the locker lumen, wherein the neck portion is configured to threadably engage the internal threads of the locker body such that rotating the locker body toward the locked position causes the collet to move in a proximal direction and rotating the locker body toward the unlocked position causes the collet to move in a distal direction.

Example 49. The delivery apparatus of any example herein, particularly any one of examples 47-48, wherein the locking mechanism is so configured that when the locker body is in the locked position, distal end portions of the arms are inserted into and compressed radially inwardly by the proximal portion of the locker lumen, and when the locker body is in the unlocked position, the distal end portions of the arms move into the distal portion of the locker lumen and expand radially outwardly.

Example 50. The delivery apparatus of any example herein, particularly any one of examples 47-49, wherein the second shaft comprises a flared portion, the flared portion having a diameter that is larger than a diameter of the opening on the end plate of the collet such that proximal movement of the second shaft is blocked when the flared portion abuts the end plate of the collet.

Example 51. A delivery apparatus for implanting a prosthetic valve comprising: a handle comprising a chamber and a stopper disposed inside the chamber; a first shaft extending from a distal end of the handle; a gripper located proximal to a proximal end of the handle; and a second shaft extending through the handle and an opening on the stopper; wherein a proximal end of the second shaft is connected to the gripper; wherein the gripper is configured to be axially moveable relative to the handle such that axial movement of the gripper causes corresponding axial movement of the second shaft relative to the first shaft and the handle; wherein the second shaft comprises a flared portion, the flared portion having a diameter that is larger than a diameter of the opening on the stopper such that proximal movement of the second shaft is blocked when the flared portion abuts the stopper.

Example 52. The delivery apparatus of any example herein, particularly example 51, wherein the handle further comprises a locking mechanism, wherein the locking mechanism comprises a rotatable locker body that is rotatable between a locked position and an unlocked position, wherein when the locker body is in the unlocked position, the second shaft and the gripper are axially moveable relative to the handle and the first shaft and wherein when the locker body is in the unlocked position, the second shaft and the gripper are not axially movable relative to the handle and the first shaft.

Example 53. The delivery apparatus of any example herein, particularly example 52, wherein an interior surface of the locker body defines a locker lumen, the locker lumen having a proximal portion and a distal portion, wherein the locker lumen has a tapered shape such that the proximal portion has a smaller diameter than the distal portion.

Example 54. The delivery apparatus of any example herein, particularly example 53, wherein the locking mechanism comprises a collet that is at least partially received within the locker lumen, wherein a distal end portion of collet comprises the stopper, wherein the collet comprises external threads engaging internal threads of the locker body and is coaxially disposed around the second shaft, wherein rotation of the locker body produces axial movement of the collet relative to the locker body and the second shaft.

Example 55. The delivery apparatus of any example herein, particularly example 54, wherein the collet comprises a neck portion extending proximally from the stopper and a plurality of arms extending proximally from the neck portion, wherein the second shaft extends through a lumen of the neck portion and the plurality of arms are disposed around the second shaft.

Example 56. The delivery apparatus of any example herein, particularly example 55, wherein the neck portion is configured to threadably engage the internal threads of the locker body such that rotating the locker body toward the locked position causes the collet to move in a proximal direction and rotating the locker body toward the unlocked position causes the collet to move in a distal direction.

Example 57. The delivery apparatus of any example herein, particularly any one of examples 55-56, wherein the locking mechanism is so configured that when the locker body is in the locked position, distal end portions of the arms are inserted into and compressed radially inwardly by the proximal portion of the locker lumen, and when the locker body is in the unlocked position, the distal end portions of the arms move into the distal portion of the locker lumen and expand radially outwardly.

Example 58. The delivery apparatus of any example herein, particularly any one of examples 52-57, wherein the locker body comprises a user-engageable portion, and the locking mechanism further comprises at least one detent element positioned to engage the user-engageable portion when the locker body is in the locked position or the unlocked position.

Example 59. The delivery apparatus of any example herein, particularly example 58, wherein the at least one detent element comprises a first detent element adjacent the locked position and a second detent element adjacent the unlocked position, wherein rotating the tab across the first detent element in a first angular direction causes the tab to align with the locked position and rotating the tab across the second detent element in a second angular direction causes the tab to align with the unlocked position, the second angular direction being opposite the first angular direction.

Example 60. The delivery apparatus of any example herein, particularly example 59, further comprising first and second biasing members respectively coupled to the first and second detent elements and configured to bias the first and second detent elements in a direction toward the user-engageable portion.

Example 61. A method for implanting a prosthetic valve, the method comprising: inserting a delivery apparatus into a vasculature of a patient, wherein the delivery apparatus comprises a handle, a first shaft extending from a distal end of the handle, and a second shaft extending through a lumen of the first shaft and the handle; wherein the prosthetic valve is crimped over a non-inflated balloon coupled to a distal end portion of the second shaft, and the prosthetic valve is covered by a valve sheath connected to a distal end portion of the first shaft; wherein a proximal end of the second shaft is connected to a gripper located proximal to a proximal end of the handle; wherein a distance from an axial axis of second shaft to a bottom surface of the gripper is substantially identical to a distance from an axial axis of the first shaft to a bottom surface of the handle.

Example 62. The method of any example herein, particularly example 61, wherein the bottom surface of the gripper and the bottom surface of the handle are substantially coplanar.

Example 63. The method of any example herein, particularly any one of examples 61-62, wherein the delivery apparatus further comprises a third shaft extending through a lumen of the second shaft, wherein a proximal end of the third shaft is connected to the gripper and a distal end of the third shaft is connected to a nosecone.

Example 64. The method of any example herein, particularly example 63, wherein a proximal end of the nosecone abuts a distal end of the valve sheath when the prosthetic valve is covered by the valve sheath.

Example 65. The method of any example herein, particularly any one of examples 63-64, wherein the balloon comprises a proximal end portion mounted on a proximal shoulder connected to a distal end portion of the second shaft, a distal end portion mounted on a distal shoulder connected to a distal end portion of the third shaft, and a valve retaining portion located between the proximal end portion and the distal end portion of the balloon, wherein the prosthetic valve is configured to be crimped over the valve retaining portion.

Example 66. The method of any example herein, particularly any one of examples 61-65, wherein the delivery apparatus further comprises an introducer mounted on the first shaft, the introducer comprising a hub and a sheath extending distally from the hub, wherein the first shaft is axially movable relative to the introducer.

Example 67. The method of any example herein, particularly example 66, wherein inserting the delivery apparatus into the vascular system comprises inserting the nosecone, the valve sheath, and the introducer together as a single unit until the sheath of the introducer is fully inserted into the vasculature, wherein a proximal end of the valve sheath abuts a distal end of the sheath of the introducer during the act of insertion.

Example 68. The method of any example herein, particularly any one of examples 61-67, further comprising navigating the delivery apparatus within the vasculature until the prosthetic valve covered by the valve sheath is positioned at a target location at or adjacent a native valve.

Example 69. The method of any example herein, particularly example 68, wherein the native valve is a pulmonary valve.

Example 70. The method of any example herein, particularly example 69, further comprising implanting a docking device at the target location before implanting the prosthetic valve, wherein the docking device is configured to receive the prosthetic valve.

Example 71. The method of any example herein, particularly example 70, wherein the docking device comprises a self-expandable frame configured to securely engage an annulus of the native valve.

Example 72. The method of any example herein, particularly any one of examples 70-71, further comprising verifying the prosthetic valve is positioned at the target location by aligning a radiopaque marker on the delivery apparatus with a predefined geometric marker of the docking device under fluoroscopy, wherein the radiopaque marker is positioned underneath the balloon.

Example 73. The method of any example herein, particularly any one of examples 69-72, wherein the handle comprises a locking mechanism, the locking mechanism comprising a locker body that is moveable between a locked position and an unlocked position, wherein when the locker body is in the unlocked position, the second shaft and the gripper are axially moveable relative to the handle and the first shaft, and wherein when the locker body is in the unlocked position, the second shaft and the gripper are not axially movable relative to the first shaft and the handle.

Example 74. The method of any example herein, particularly example 73, further comprising moving the locker body to the locked position before inserting the delivery apparatus into the vasculature.

Example 75. The method of any example herein, particularly any one of examples 73-74, further comprising moving the locker body to the unlocked position after the prosthetic valve is positioned at the target location.

Example 76. The method of any example herein, particularly example 75, further comprising unsheathing the prosthetic valve by keeping the gripper stationary while moving the handle proximally toward the gripper so that the valve sheath and the first shaft move proximally relative to the second shaft and the prosthetic valve, thereby exposing at least a portion of the prosthetic valve.

Example 77. The method of any example herein, particularly example 76, wherein unsheathing the prosthetic valve comprises moving the handle proximally until the proximal end of the handle contacts the gripper such that the prosthetic valve is completely uncovered by the valve sheath.

Example 78. The method of any example herein, particularly any one of examples 76-77, further comprising inflating the balloon so as to radially expand the prosthetic valve.

Example 79. The method of any example herein, particularly example 78, further comprising resheathing the balloon after the balloon is deflated by keeping the handle stationary while moving the gripper axially so that the second shaft and the balloon move proximally relative to the valve sheath and the first sheath, thereby covering at least a portion of the balloon with the valve sheath.

Example 80. The method of any example herein, particularly example 79, wherein resheathing the balloon comprises moving the gripper proximally relative to the handle until a proximal end of the nosecone contacts a distal end of the valve sheath such that the balloon is completely covered by the valve sheath.

Example 81. The method of any example herein, particularly any one of examples 66-80, further comprising retracting the delivery apparatus by moving the first shaft and the valve sheath proximally until the proximal end of the valve sheath contacts a distal end of the sheath of the introducer, and then retracting the introducer, the first shaft, and the valve sheath together as a single unit out of the vasculature.

Example 82. The method of any example herein, particularly any one of examples 61-81, wherein the delivery apparatus further comprises a fourth shaft extending through the handle, wherein a proximal end of the fourth shaft is connected to the gripper, wherein the fourth shaft comprises a flared portion, the flared portion having a diameter that is larger than a diameter of an opening of a stopper disposed inside the handle such that proximal movement of the gripper is blocked when the flared portion abuts the stopper.

Example 83. An assembly comprising: a radially expandable and compressible prosthetic valve; and a delivery apparatus comprising a handle, a gripper located proximal to a proximal end of the handle, a first shaft extending from a distal end of the handle, and a second shaft extending through a lumen of the first shaft and the handle, a proximal end of the second shaft being connected to the gripper; wherein the prosthetic valve is mounted over an inflatable balloon coupled to a distal end portion of the second shaft; wherein the handle comprises a locking mechanism, the locking mechanism comprising a locker body having a user-engageable portion, wherein the locker body is moveable between a locked position and an unlocked position, wherein when the locker body is in the unlocked position, the gripper is axially moveable relative to the handle, and wherein when the locker body is in the unlocked position, the gripper is not axially movable relative to the handle; wherein the user-engagement portion is configured to engage at least one detent element when the locker body is in the locked position or unlocked position.

Example 84. The assembly of any example herein, particularly example 83, further comprising a valve sheath connected to a distal end portion of the first shaft, wherein the valve sheath is configured to cover the prosthetic valve in a radially compressed configuration.

Example 85. The assembly of any example herein, particularly example 84, further comprising a third shaft extending through a lumen of the second shaft, wherein a proximal end of the third shaft is connected to the gripper and a distal end of the third shaft is connected to a nosecone.

Example 86. The assembly of any example herein, particularly example 85, wherein a proximal end of the nosecone abuts a distal end of the valve sheath when the prosthetic valve is covered by the valve sheath.

Example 87. The assembly of any example herein, particularly any one of examples 84-86, further comprising an introducer mounted on the first shaft, the introducer comprising a sheath and a hub connected to a proximal end of the sheath, wherein the first shaft extends through and is axially movable relative to the sheath and the hub.

Example 88. The assembly of any example herein, particularly any one of examples 83-87, further comprising a fourth shaft extending through the handle, wherein a proximal end of the fourth shaft is connected to the gripper and the second shaft extends through the fourth shaft.

Example 89. The delivery apparatus of any example herein, particularly example 88, wherein the fourth shaft comprises a flared portion, the flared portion having a diameter that is larger than a diameter of an opening of a stopper disposed inside the handle such that proximal movement of the gripper is blocked when the flared portion abuts the stopper.

Example 90. The delivery apparatus of any example herein, particularly any one of examples 88-89, wherein the fourth shaft is more rigid than the second shaft.

Example 91. The delivery apparatus of any example herein, particularly any one of examples 88-90, wherein the gripper further comprises a Y-connector having a first port, a second port, and a third port, wherein the second shaft, the third shaft, and the fourth shaft are connected to the first port.

Example 92. The delivery apparatus of any example herein, particularly example 91, wherein the first port is located at a distal portion of the gripper, the second port extends out of a proximal opening of the gripper, and the third port extends out of an upper opening of the gripper.

In view of the many possible embodiments to which the principles of the disclosed technology may be applied, it should be recognized that the illustrated embodiments are only representative examples of the disclosed technology and should not be taken as limiting the scope of the disclosed technology. Rather, the scope of the disclosed technology is defined by the following claims.

We claim:

1. A delivery apparatus for implanting a prosthetic valve comprising:

a handle;

a first shaft extending from a distal end of the handle;

a second shaft extending through a lumen of the first shaft and the handle; and a gripper located proximal to a proximal end of the handle;

wherein a proximal end of the second shaft is connected to the gripper, and the gripper is axially moveable relative to the handle such that axial movement of the gripper causes corresponding axial movement of the second shaft relative to the first shaft;

wherein the gripper has a bottom surface that is substantially coplanar with a bottom surface of the handle, wherein a distance from a longitudinal axis of the second shaft to the bottom surface of the gripper is substantially identical to a distance from a longitudinal axis of the first shaft to the bottom surface of the handle, wherein the gripper comprises opposed, first and second side surfaces, wherein the gripper and the second shaft are rotatable relative to the handle, wherein the distance from the longitudinal axis of the second shaft to the bottom surface of the gripper is the same as a distance from the longitudinal axis of the second shaft to the first side surface and the same as a distance from the longitudinal axis of the second shaft to the second side surface.

2. The delivery apparatus of claim 1, wherein the first shaft comprises a proximal section, a distal section, and an intermediate section between the proximal and distal sections, wherein the distal section is more flexible than the intermediate section and the intermediate section is more flexible than the proximal section.

3. The delivery apparatus of claim 1, further comprising an inflatable balloon, the balloon having a valve retaining portion configured to mount the prosthetic valve thereto.

4. The delivery apparatus of claim 3, further comprising a valve sheath configured to cover the prosthetic valve when the prosthetic valve is mounted on the balloon in a radially compressed state, wherein a proximal end of the valve sheath is connected to a distal end of the first shaft.

5. The delivery apparatus of claim 4, wherein when the prosthetic valve is covered by the valve sheath, a distance between the proximal end of the handle and the gripper is equal to or greater than a length of the valve sheath such that when the proximal end of the handle contacts the gripper after axially moving the handle relative to the gripper, a distal end of the valve sheath is located proximal to a proximal end of the prosthetic valve, thereby completely uncovering the prosthetic valve.

6. The delivery apparatus of claim 4, further comprising a third shaft extending through a lumen of the second shaft, wherein a proximal end of the third shaft is connected to the gripper and a distal end of the third shaft is connected to a nosecone.

7. The delivery apparatus of claim 6, further comprising a balloon shoulder assembly, wherein the balloon shoulder assembly comprises a proximal shoulder connected to a distal end portion of the second shaft and a distal shoulder connected to a distal end portion of the third shaft, wherein the distal and proximal shoulders are disposed inside the balloon.

8. The delivery apparatus of claim 7, wherein the third shaft comprises a radiopaque marker located between the proximal shoulder and the distal shoulder.

9. The delivery apparatus of claim 6, wherein a proximal end of the nosecone abuts a distal end of the valve sheath when the prosthetic valve is retained inside the valve sheath.

10. The delivery apparatus of claim 1, wherein the gripper comprises a housing defining the bottom surface of the gripper, the gripper further comprising a Y-connector having a main tubular portion and a side tubular portion, the side tubular portion being fluidly connected to and extending angularly from the main tubular portion, wherein the main tubular portion extends through the gripper housing and is substantially parallel to the bottom surface of the gripper housing, and the side tubular portion extends through an opening on top surface of the gripper housing.

11. The delivery apparatus of claim 10, wherein the proximal end of the second shaft is connected to the main tubular portion of the Y-connector.

12. The delivery apparatus of claim 1, further comprising an introducer mounted on the first shaft, the introducer comprising a sheath and a hub connected to a proximal end of the sheath, wherein the first shaft extends through and is axially movable relative to the sheath and the hub.

13. The delivery apparatus of claim 1, further comprising a third shaft extending through the handle, wherein a proximal end of the third shaft is connected to the gripper and the second shaft extends through the third shaft.

14. The delivery apparatus of claim 13, wherein the handle comprises a locking mechanism, the locking mechanism comprising a locker body that is moveable between a locked position and an unlocked position, wherein when the locker body is in the unlocked position, the second and third shafts are axially moveable relative to the handle and the first shaft, and wherein when the locker body is in the locked position, the second and third shafts are not axially movable relative to the first shaft and the handle.

15. The delivery apparatus of claim 14, wherein the locker body comprises a user-engageable tab, wherein the locking mechanism further comprises at least one detent element positioned to engage the tab when the locker body is in the locked position or the unlocked position.

16. The delivery apparatus of claim 15, wherein the at least one detent element comprises a first detent element adjacent the locked position and a second detent element adjacent the unlocked position, wherein rotating the tab across the first detent element in a first angular direction causes the tab to align with the locked position and rotating the tab across the second detent element in a second angular direction causes the tab to align with the unlocked position, the second angular direction being opposite the first angular direction.

17. The delivery apparatus of claim 14, wherein the locking mechanism further comprises a collet that is at least partially received within the locker body, wherein the collet comprises external threads engaging internal threads of the locker body and is coaxially disposed around the third shaft, wherein rotation of the locker body produces axial movement of the collet relative to the locker body and the third shaft.

18. The delivery apparatus of claim 17, wherein the collet has a distal opening through which the third shaft extends, the third shaft comprises a flared portion, wherein the flared portion has a diameter that is larger than a diameter of the distal opening such that proximal movement of the third shaft is blocked when the flared portion abuts the collet.

19. The delivery apparatus of claim 14, wherein an interior surface of the locker body defines a locker lumen, the locker lumen having a proximal portion and a distal portion, wherein the locker lumen has a tapered shape such that the proximal portion has a smaller diameter than the distal portion.

20. The delivery apparatus of claim 1, wherein the bottom surface of the gripper and the bottom surface of the handle are coplanar with a plane that is parallel to the longitudinal axis of the first shaft and the longitudinal axis of the second shaft.

21. The delivery apparatus of claim 20, wherein the bottom surface of the gripper comprises a flat bottom surface portion.

22. The delivery apparatus of claim 21, wherein the first side surface comprises a first flat side surface portion and the second side surface comprises a second flat side surface portion wherein when the gripper is rotated to a position with the first flat side surface portion facing downwardly, the first flat side surface portion is coplanar with the bottom surface of the handle, and wherein when gripper is rotated to another position with the second flat side surface portion facing downwardly, the second flat side surface is coplanar with the bottom surface of the handle.

* * * * *